United States Patent
Busch et al.

(10) Patent No.: US 10,759,153 B2
(45) Date of Patent: Sep. 1, 2020

(54) FLEXIBLE BONDING

(71) Applicant: The Procter & Gamble Company, Cincinnati, OH (US)

(72) Inventors: James W. Busch, Maineville, OH (US); Jennifer L. Schallick, Guilford, IN (US); Stephen D. Congleton, Loveland, OH (US); Dale F. Bittner, Harrison, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 16/211,290

(22) Filed: Dec. 6, 2018

(65) Prior Publication Data

US 2019/0176450 A1    Jun. 13, 2019

Related U.S. Application Data

(60) Provisional application No. 62/595,606, filed on Dec. 7, 2017.

(51) Int. Cl.
*B32B 37/00* (2006.01)
*B32B 38/06* (2006.01)
(Continued)

(52) U.S. Cl.
CPC .... *B32B 37/0053* (2013.01); *A61F 13/15699* (2013.01); *A61F 13/15739* (2013.01); *A61F 13/15764* (2013.01); *A61F 13/49* (2013.01); *B29C 65/02* (2013.01); *B29C 66/21* (2013.01); *B29C 66/234* (2013.01); *B29C 66/45* (2013.01); *B29C 66/81433* (2013.01); *B29C 66/81453* (2013.01); *B29C 66/83413* (2013.01); *B29C 66/924* (2013.01); *B32B 38/06* (2013.01); *B33Y 80/00* (2014.12); *A61F 2013/15715* (2013.01);
(Continued)

(58) Field of Classification Search
None
See application file for complete search history.

(56) References Cited

U.S. PATENT DOCUMENTS

| 4,854,984 A | 8/1989 | Ball et al. |
| 5,167,897 A | 12/1992 | Weber et al. |

(Continued)

FOREIGN PATENT DOCUMENTS

| EP | 0 295 957 A1 | 12/1988 | |
| GB | 726885 A | * 3/1955 | ....... B29C 66/81611 |

(Continued)

OTHER PUBLICATIONS

15041M PCT International Search Report, dated Feb. 15, 2019, 13 pages.

*Primary Examiner* — Barbara J Musser
(74) *Attorney, Agent, or Firm* — C. Brant Cook

(57) ABSTRACT

A flexible bonding roll including one or more pressure applying members is configured to operatively engage an anvil roll. The one or more pressure applying members include one or more spring elements. The spring elements allow for the one or more pressure applying members to compress as the pressure applying members are engaged by the outer circumferential surface of the anvil roll. The compression of the pressure applying members allows for relatively reduced damage of substrates and equipment during bonding.

12 Claims, 19 Drawing Sheets

(51) Int. Cl.
*A61F 13/15* (2006.01)
*A61F 13/49* (2006.01)
*B29C 65/00* (2006.01)
*B29C 65/02* (2006.01)
*B33Y 80/00* (2015.01)

(52) U.S. Cl.
CPC ............... *A61F 2013/15861* (2013.01); *B32B 2307/726* (2013.01); *B32B 2555/02* (2013.01)

(56) References Cited

U.S. PATENT DOCUMENTS

| | | | |
|---|---|---|---|
| 5,360,420 A | 11/1994 | Cook et al. | |
| 5,599,335 A | 2/1997 | Goldman et al. | |
| 5,628,097 A | 5/1997 | Benson et al. | |
| 5,643,588 A | 7/1997 | Roe et al. | |
| 5,674,216 A | 10/1997 | Buell et al. | |
| 5,702,551 A | 12/1997 | Huber et al. | |
| D409,343 S | 5/1999 | Kingry et al. | |
| 5,968,025 A | 10/1999 | Roe et al. | |
| 6,003,191 A | 12/1999 | Sherry et al. | |
| D423,742 S | 4/2000 | Kingry et al. | |
| 6,107,537 A | 8/2000 | Elder et al. | |
| 6,118,041 A | 9/2000 | Roe et al. | |
| 6,153,209 A | 11/2000 | Vega et al. | |
| 6,166,117 A | 12/2000 | Miyazai et al. | |
| 6,305,046 B1 | 10/2001 | Kingry et al. | |
| 6,410,129 B2 | 6/2002 | Zhang et al. | |
| 6,426,444 B2 | 7/2002 | Roe et al. | |
| 6,484,346 B2 | 11/2002 | Kingry et al. | |
| 6,561,354 B1 | 5/2003 | Fereshtehkhou et al. | |
| 6,586,652 B1 | 7/2003 | Roe et al. | |
| 6,601,261 B1 | 8/2003 | Holt et al. | |
| 6,617,016 B2 | 9/2003 | Zhang et al. | |
| 6,627,787 B1 | 9/2003 | Roe et al. | |
| 6,645,190 B1 | 11/2003 | Olson et al. | |
| 6,645,604 B1 | 11/2003 | Fereshtehkhou et al. | |
| 6,651,290 B2 | 11/2003 | Kingry et al. | |
| D489,537 S | 5/2004 | Wong et al. | |
| 6,761,711 B1 | 7/2004 | Fletcher et al. | |
| 6,777,064 B1 | 8/2004 | Fereshtehkhou et al. | |
| 6,787,512 B1 | 9/2004 | Verrall et al. | |
| 6,790,794 B2 | 9/2004 | Fereshtehkhou et al. | |
| 6,797,357 B2 | 9/2004 | Fereshtehkhou et al. | |
| D498,930 S | 11/2004 | Wong et al. | |
| 6,817,994 B2 | 11/2004 | Popp et al. | |
| 6,825,393 B2 | 11/2004 | Roe et al. | |
| D499,887 S | 12/2004 | Wong et al. | |
| 6,840,928 B2 | 1/2005 | Datta et al. | |
| D501,609 S | 2/2005 | Wong et al. | |
| 6,849,067 B2 | 2/2005 | Fletcher et al. | |
| 6,861,571 B1 | 3/2005 | Roe et al. | |
| 6,893,426 B1 | 5/2005 | Popp et al. | |
| 6,936,330 B2 | 8/2005 | Fereshtehkhou et al. | |
| 6,953,452 B2 | 10/2005 | Popp et al. | |
| D511,251 S | 11/2005 | Wong | |
| 6,969,377 B2 | 11/2005 | Koele et al. | |
| 7,156,833 B2 | 1/2007 | Couture-Dorschner et al. | |
| 7,201,744 B2 | 4/2007 | Van Gompel et al. | |
| 7,219,386 B2 | 5/2007 | Tsuchiya et al. | |
| 7,293,317 B2 | 11/2007 | Tsuchiya et al. | |
| 7,383,602 B2 | 6/2008 | Tanaka et al. | |
| 7,497,851 B2 | 3/2009 | Koele et al. | |
| 7,682,349 B2 | 3/2010 | Popp et al. | |
| D615,378 S | 5/2010 | Koenig | |
| 7,803,726 B2 | 9/2010 | Policicchio et al. | |
| 7,862,550 B2 | 1/2011 | Koele et al. | |
| 7,901,393 B2 | 3/2011 | Matsuda et al. | |
| 8,007,485 B2 | 8/2011 | Popp et al. | |
| 8,361,048 B2 | 1/2013 | Kuen et al. | |
| 8,372,052 B2 | 2/2013 | Popp et al. | |
| 8,578,564 B2 | 11/2013 | Policicchio et al. | |
| 8,579,876 B2 | 11/2013 | Popp et al. | |
| 8,747,379 B2 | 6/2014 | Fletcher et al. | |
| 8,756,746 B2 | 6/2014 | Policicchio et al. | |
| 8,763,197 B2 | 7/2014 | Policicchio et al. | |
| 8,931,132 B2 | 1/2015 | Policicchio | |
| 9,421,137 B2 | 8/2016 | LaVon et al. | |
| 9,498,389 B2 | 12/2016 | Trennepohl et al. | |
| 2006/0213801 A1 | 9/2006 | Karaoren et al. | |
| 2010/0233438 A1 | 9/2010 | Stone et al. | |
| 2010/0233439 A1 | 9/2010 | Stone et al. | |
| 2011/0186468 A1 | 8/2011 | Denome et al. | |
| 2011/0188784 A1 | 8/2011 | Denome et al. | |
| 2013/0211363 A1 | 8/2013 | LaVon et al. | |
| 2014/0005020 A1 | 1/2014 | LaVon et al. | |
| 2014/0377506 A1 | 12/2014 | Eckstein et al. | |
| 2014/0377513 A1 | 12/2014 | Galie et al. | |
| 2015/0173961 A1 | 6/2015 | Powell et al. | |
| 2016/0136014 A1 | 5/2016 | Arora et al. | |
| 2018/0221214 A1 | 8/2018 | Eckstein et al. | |
| 2018/0318143 A1 | 11/2018 | Galie et al. | |

FOREIGN PATENT DOCUMENTS

| | | | |
|---|---|---|---|
| GB | 2504783 A | * 2/2014 | ............ B29C 66/21 |
| WO | WO 2002042408 | 5/2002 | |
| WO | WO 2009098659 | 8/2009 | |
| WO | WO 2010119022 | 10/2010 | |
| WO | WO 2014/204736 A1 | 12/2014 | |
| WO | WO 2014/204744 A1 | 12/2014 | |

* cited by examiner

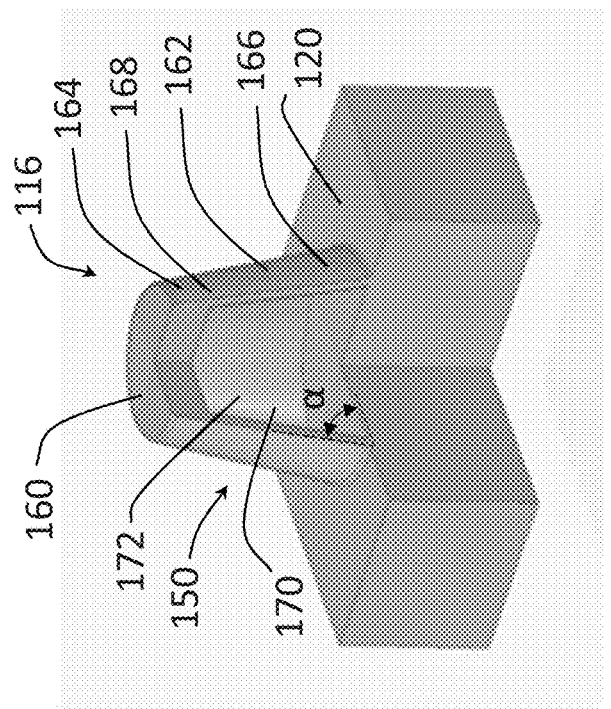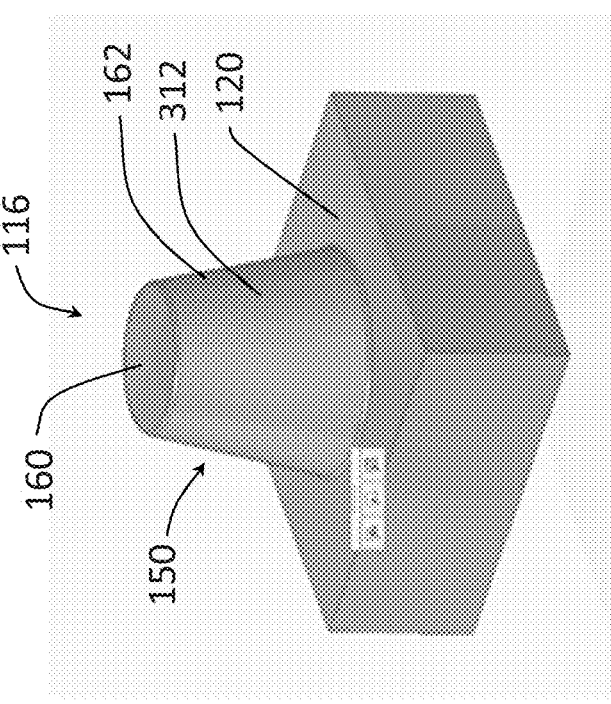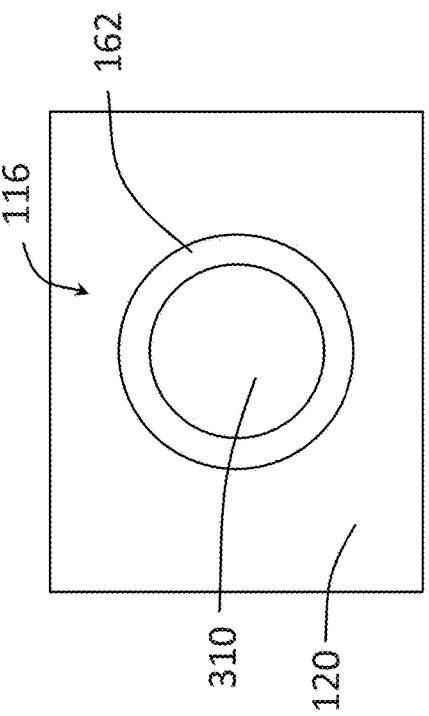

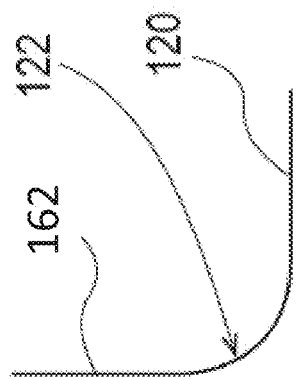
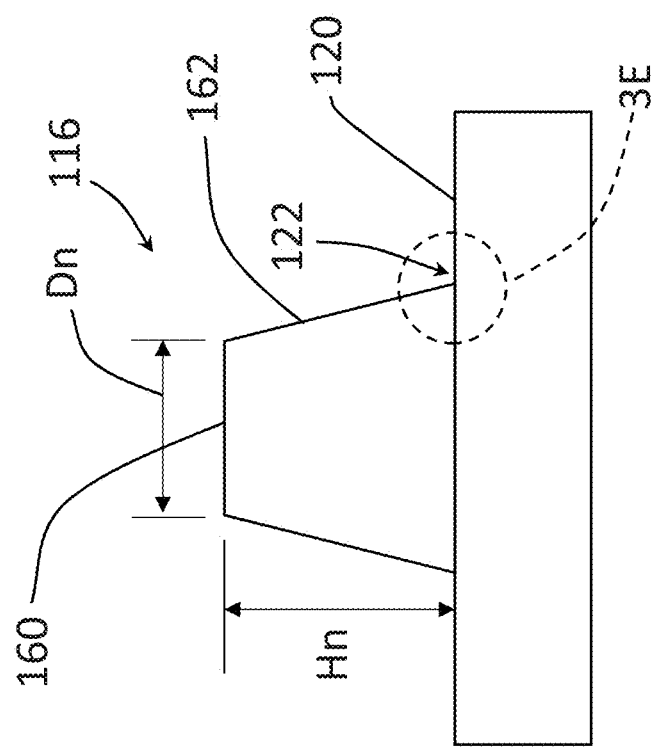

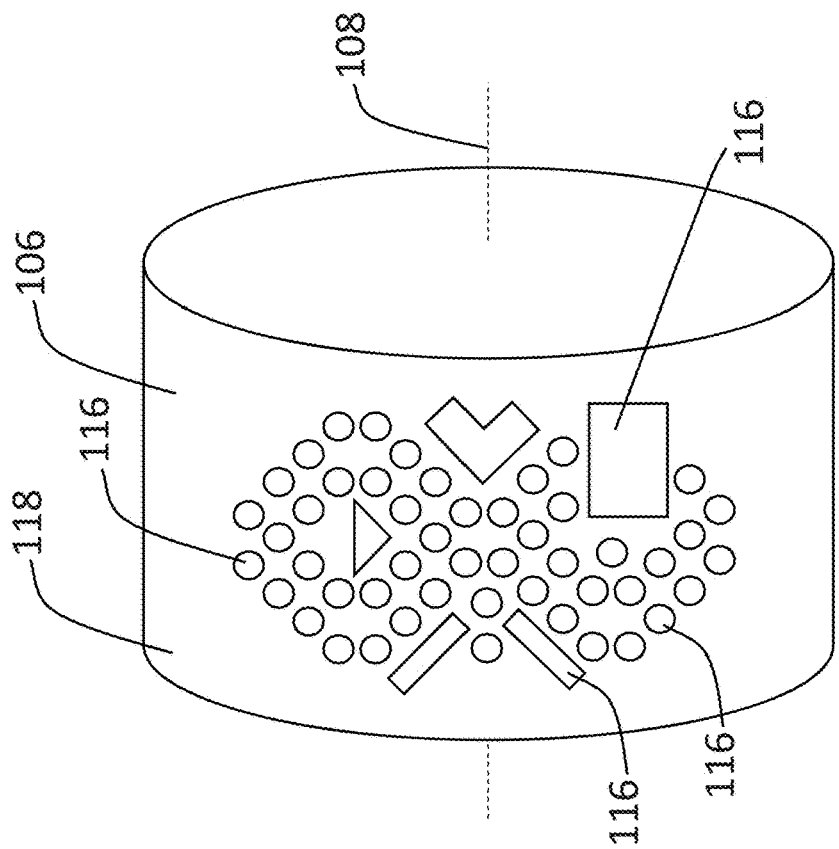
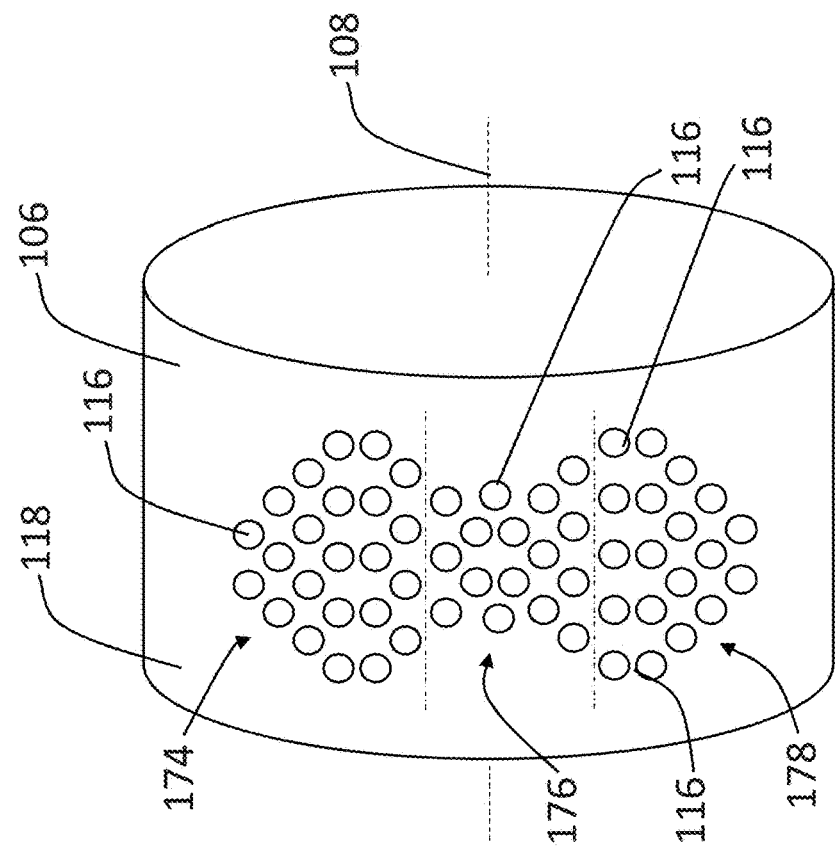

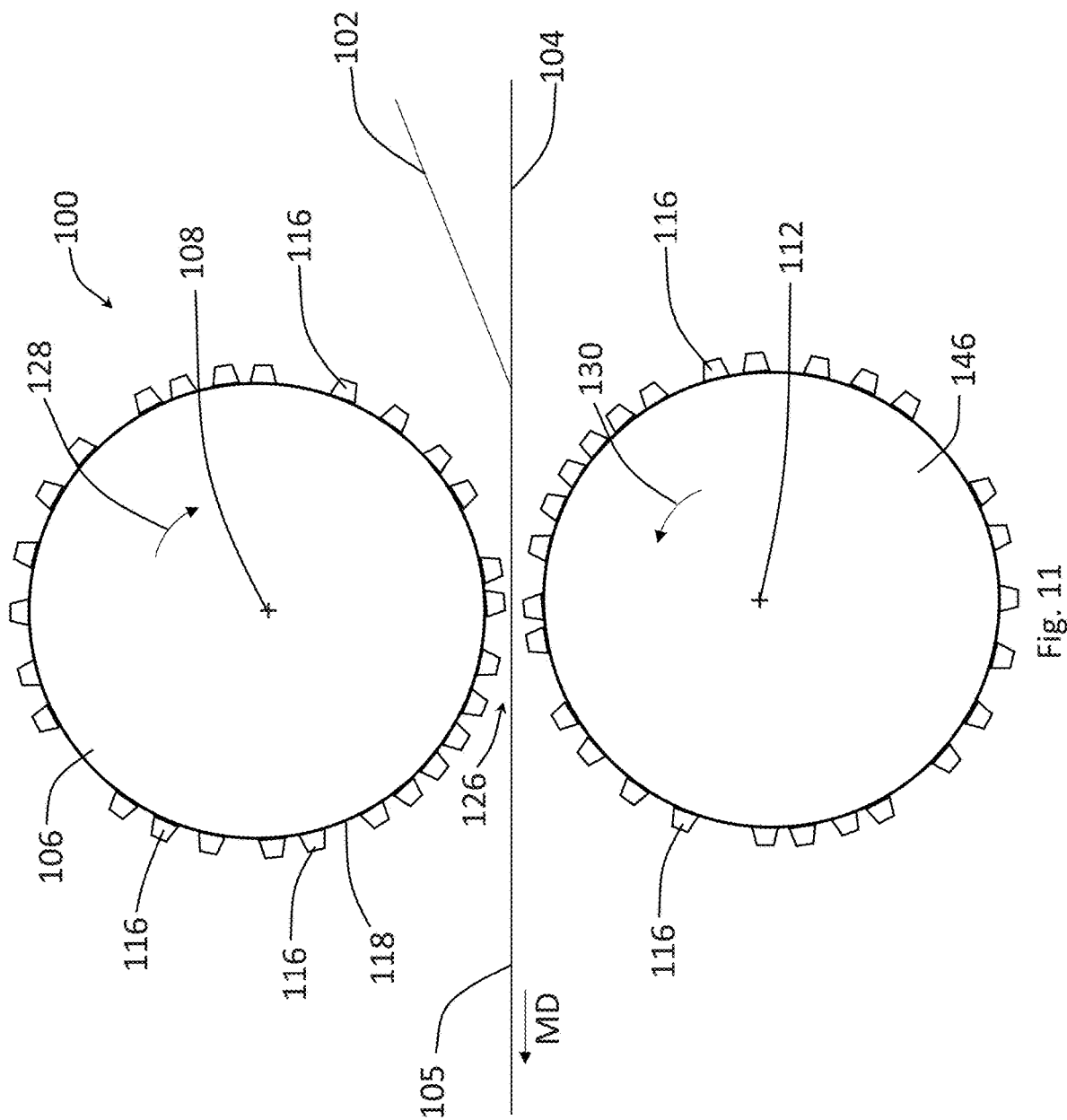

FLEXIBLE BONDING

FIELD

The present disclosure relates to apparatuses and methods for bonding absorbent article component substrates advancing in a machine direction, and more particularly, methods and apparatuses including an anvil roll and a bonding roll with one or more pressure applying members.

BACKGROUND

Along an assembly line, various types of articles, for example sanitary napkins, diapers, and other absorbent articles, may be assembled by adding components to and/or otherwise modifying an advancing, continuous web of material. For example, in some processes, advancing webs of material are combined with other advancing webs of material. In other examples, individual components created from advancing webs of material are combined with advancing webs of material, which in turn, are then combined with other advancing webs of material. In some cases, individual components created from advancing web or webs are combined with other individual components created from other advancing web or webs. Webs of material and component parts used to manufacture diapers may include: backsheets, topsheets, leg cuffs, waist bands, absorbent core components, front and/or back ears, fastening components, and various types of elastic webs and components such as leg elastics, barrier leg cuff elastics, stretch side panels, and waist elastics. Webs of material and component parts used to manufacture sanitary napkins may include: backsheets, topsheets, secondary topsheets, absorbent core components, release paper wrappers, and the like. Once the desired component parts are assembled, the advancing web(s) and component parts are subjected to a final knife cut to separate the web(s) into discrete articles.

During the assembly process, various components and/or advancing webs of material may be bonded together in various ways. For example, in some processes, advancing webs and/or components may be bonded together with adhesives. In other processes, advancing webs and/or components may be mechanically bonded together with heat and/or pressure without the use of adhesives. An example of such a mechanical bonding method and apparatus is disclosed in U.S. Pat. No. 4,854,984, wherein two laminates are bonded together by advancing through a nip between a patterned cylinder and an anvil cylinder. Pattern elements on the patterned cylinder exert pressure on the two laminates against the anvil roll to create discrete bond sites. More particularly, bond sites are created as the extreme nip pressure compresses and yields the laminate material in areas between the pattern elements and the anvil. During the bonding process, some of the yielded material may flow from the bond site to areas surrounding the perimeter of the pattern element.

These mechanical bonding methods may damage the resultant laminate web by forming holes and/or tears in or around the bond sites. For example, pattern elements may comprise sharp edges and may tear, cut, or weaken the bonded web in areas adjacent to the bonds. Tears may propagate from one bond site to another, causing a zippering of the web. This often creates a consumer-noticeable defective product. In addition, as the web basis weight of the laminate decreases, bonds may become more susceptible to bond defects such as tearing and holes at relatively high nip pressures.

Consequently, it would be beneficial to provide a method and apparatus for mechanically bonding substrates that produces bond sites with relatively low likelihood of damage to the substrate. Previous attempts to address these problems are not desirable due to cost and complexity. There is a desire for bonding with pressure applying members which minimize the applied process strain on a substrate, so that this applied process strain is less than the failure strain of the substrate of interest. There is a need to reduce or eliminate substrate damage, such as tearing and holes, as a result of bonding.

SUMMARY

The present disclosure relates to methods and apparatuses for bonding absorbent article component substrates advancing in a machine direction, and more particularly, methods and apparatuses including an anvil roll and a bonding roll with one or more pressure applying members. In some embodiments, a method for forming a bond includes: rotating a bonding roll about an axis of rotation, the bonding roll comprising a first pressure applying member extending radially outward from the bonding roll, wherein the first pressure applying member comprises a first spring element; rotating an anvil roll adjacent the bonding roll such that a nip is formed between the bonding roll and the anvil roll; advancing a first substrate in a machine direction through the nip; rotating the bonding roll and the anvil roll wherein the first pressure applying member compresses at least a portion of the first substrate forming a bond; and compressing the first pressure applying member by a first compression distance.

In some embodiments, an apparatus for bonding substrate includes an anvil roll, and a bonding roll positioned adjacent the anvil roll. The bonding roll may include a first portion, a second portion, and plurality of pressure applying members. The plurality of pressure applying members may include a first group of pressure applying members and a second group of pressure applying members. Each of the first group of pressure applying members may include a first spring element. Each of the second group of pressure applying members may include a second spring element. Further, the first group of pressure applying members may be disposed on the first portion of the bonding roll, and the second group of pressure applying members are disposed on the second portion of the bonding roll. The anvil roll operatively engages each of the first group of pressure applying members and the second group of pressure applying members. The first group of pressure applying members may compress by a first compression distance, and the second group of pressure applying members may compress by a second compression distance. The first compression distance may be different than the second compression distance.

In some embodiments, an apparatus for bonding substrate may include an anvil roll and a bonding roll positioned adjacent the anvil roll. The bonding roll may include an outer circumferential surface, a first bonding surface opposite to the outer circumferential surface, and an inner circumferential surface positioned radially inward of the outer circumferential surface. Further, a plurality of pressure applying members may be joined to the outer circumferential surface of the bonding roll. A plurality of spring elements may be disposed between the first bonding surface and the inner circumferential surface. Each of the plurality of spring elements have a spring constant, wherein the spring constants among the plurality of spring elements are variable.

BRIEF DESCRIPTION OF THE DRAWINGS

FIG. 3A is a perspective view of a pressure applying member;
FIG. 3B is a perspective view of a pressure applying member including a cut-out portion;
FIG. 3C is a top view of a pressure applying member;
FIG. 3D is a side view of a pressure applying member;
FIG. 3E is a portion of a pressure applying member including the spring element and the base surface;
FIG. 8 is a perspective view of a bonding roll including a plurality of pressure applying members;
FIG. 9 is a perspective view of a bonding roll including a plurality of pressure applying members;
FIG. 11 is a side view of a bonding apparatus.

DETAILED DESCRIPTION

Figure 1A:
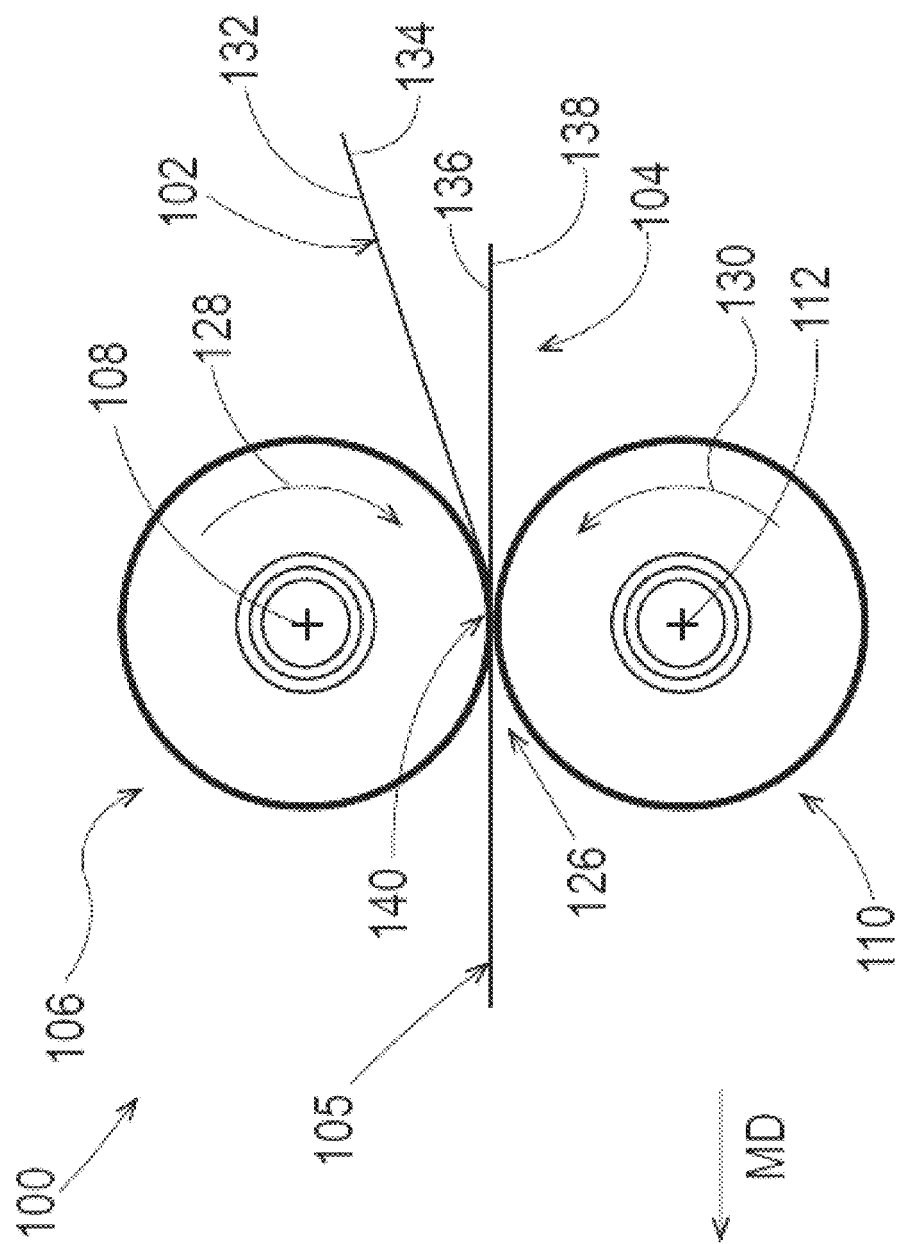
FIG. 1A is a side view of a bonding apparatus.

As used herein, the term "absorbent article" includes disposable articles such as sanitary napkins, panty liners, tampons, interlabial devices, wound dressings, diapers, adult incontinence articles, wipes, and the like. At least some of such absorbent articles are intended for the absorption of body liquids, such as menses or blood, vaginal discharges, urine, and feces. Wipes may be used to absorb body liquids, or may be used for other purposes, such as for cleaning surfaces. Various absorbent articles described above will typically comprise a liquid pervious topsheet, a liquid impervious backsheet joined to the topsheet, and an absorbent core between the topsheet and backsheet.

The term "pant" (also referred to as "training pant", "pre-closed diaper", "diaper pant", "pant diaper", and "pull-on diaper") refers herein to disposable absorbent articles having a continuous perimeter waist opening and continuous perimeter leg openings designed for infant or adult wearers. A pant can be configured with a continuous or closed waist opening and at least one continuous, closed, leg opening prior to the article being applied to the wearer. A pant can be preformed by various techniques including, but not limited to, joining together portions of the article using any refastenable and/or permanent closure member (e.g., seams, heat bonds, pressure welds, adhesives, cohesive bonds, mechanical fasteners, etc.). A pant can be preformed anywhere along the circumference of the article in the waist region (e.g., side fastened or seamed, front waist fastened or seamed, rear waist fastened or seamed.

The term "taped diaper" refers to disposable absorbent articles having an initial front waist region and an initial rear waist region that are not fastened, pre-fastened, or connected to each other as packaged, prior to being applied to the wearer. A taped diaper may be folded about its lateral central axis with the interior of one waist region in surface to surface contact with the interior of the opposing waist region without fastening or joining the waist regions together. Example taped diapers disclosed in various suitable configurations are disclosed in U.S. Pat. Nos. 5,167,897; 5,360,420; 5,599,335; 5,643,588; 5,674,216; 5,702,551; 5,968,025; 6,107,537; 6,118,041; 6,153,209; 6,410,129; 6,426,444; 6,586,652; 6,627,787; 6,617,016; 6,825,393; and 6,861,571.

As used herein, the term "pressure applying member" refers to any element on the surface of a roll that is capable of bonding two or more substrates.

As used herein, the term "joined" encompasses configurations whereby an element is directly secured to another element by fixedly attaching or removably attaching the element directly to the other element, and configurations whereby an element is indirectly secured to another element by fixedly attaching or removably attaching the element to intermediate member(s) which in turn are fixedly attached or removably attached to the other element.

The term "substrate" is used herein to describe a material which is primarily two-dimensional (i.e. in an XY plane) and whose thickness (in a Z direction) is relatively small (i.e. ¹⁄₁₀ or less) in comparison to its length (in an X direction) and width (in a Y direction). Non-limiting examples of substrates include a web, layer or layers or fibrous materials, nonwovens, films, and foils such as polymeric films or metallic foils. These materials may be used alone or may comprise two or more layers laminated together (a "composite substrate"). As such, a web is a substrate.

The term "nonwoven" refers herein to a material made from continuous (long) filaments (fibers) and/or discontinuous (short) filaments (fibers) by processes such as spunbonding, meltblowing, carding, and the like. Nonwovens do not have a woven or knitted filament pattern.

The term "machine direction" (MD) is used herein to refer to the direction of material flow through a process. In addition, relative placement and movement of material may be described as flowing in the machine direction through a process from upstream in the process to downstream in the process.

The term "cross direction" (CD) is used herein to refer to a direction that is generally perpendicular to the machine direction.

"Z-direction" as used herein, is the direction perpendicular to both the machine and cross directions.

The term "yield" is used herein to refer to permanent and non-reversible material displacement due to subjecting the material to mechanical stress past the yield stress of the material and/or permanent and non-reversible material displacement due to subjecting the material to temperatures higher than the melting point of the material.

The term "ultimate" is used herein to refer to material failure due to subjecting the material to mechanical stress past the ultimate stress of the material.

The present disclosure relates to methods and apparatuses for manufacturing absorbent articles, and in particular, to methods and apparatuses for mechanically bonding substrates together. It is to be appreciated that bonding includes embossing, which may be performed at a lower force or pressure on the material that consolidates or entangles the material. The apparatuses may include a bonding roll and an anvil roll. The bonding roll may include a plurality of bonding elements, or pressure applying members, protruding radially outward, wherein each pressure applying member includes a bonding surface. And the bonding roll may be adjacent the anvil roll to define a nip between the bonding surfaces and the anvil roll. The bonding roll may be biased toward the anvil roll to define a nip pressure between bonding surfaces and the anvil roll. As the first and second substrates advance between the bonding roll and anvil roll, the first substrate and the second substrate are compressed between the anvil roll and the bonding surfaces of the pressure applying members to form a discrete bond region between the first and second substrates. More particularly, during the bonding process, the nip pressure causes the first and second substrate materials to yield. And the yielded materials are pressed together to form a bond region. It is to be appreciated that one or more substrate may undergo bonding. For example, a single substrate may undergo bonding, a single substrate that has been folded may undergo bonding, or two or more substrates overlapping a portion of one another may undergo bonding. Further, where at least two materials, such as two layers or two substrates, are to be bonded, the material with the lower yield may be forced into and between the structure of the higher yield material(s) forming a bond where the materials are entangled.

It is to be appreciated that various arrangements and configurations of the apparatuses and methods herein may be used to bond various types of substrates together. For example, as discussed in more detail below, apparatuses and methods according to the present disclosure may be utilized to bond various substrates together during the production of various components of absorbent articles, such as sanitary napkins, incontinence articles, diapers, toilet tissue, paper towels, and facial tissue.

Figure 1B:
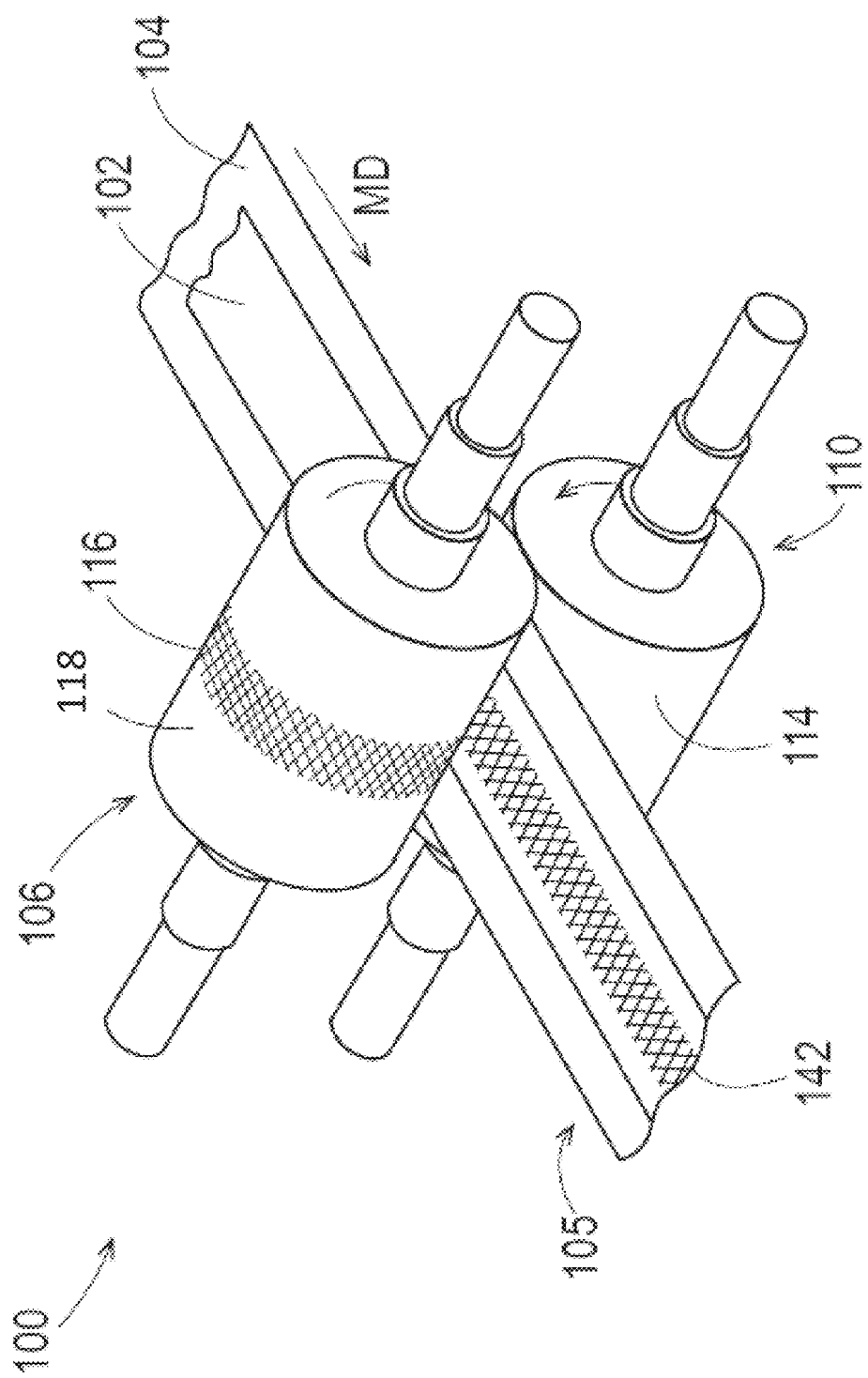
FIG. 1B is a perspective view of a bonding apparatus.

FIGS. 1A and 1B illustrate an embodiment of a bonding apparatus 100 that may be used to bond a single substrate or a first substrate 102 and a second substrate 104 to form a laminate 105. The bonding apparatus 100 may include a bonding roll 106 adapted to rotate around an axis of rotation 108, and an anvil roll 110 adapted to rotate around an axis of rotation 112. As shown in FIG. 1B, the anvil roll 110 includes an outer circumferential surface 114 which is preferably smooth, and the bonding roll 106 includes an outer circumferential surface 118 and one or more bonding elements, or pressure applying members, 116. The one or more bonding elements, also referred to herein as pressure applying members 116, may extend radially away from the outer circumferential surface 118 of the bonding roll 106. Further, the bonding roll 106 may include any number of pressure applying members 116 based on the desired bonding pattern. The bonding roll 106 is adjacent the anvil roll 110 so as to define a nip 126 between the bonding roll 106 and the anvil roll 110, and more particularly, to define a nip 126 between the bonding surface of each pressure applying member 116 and the anvil roll 110. It is to be appreciated that the bonding roll 106 and the anvil roll 110 may be configured to rotate such that the bonding surfaces on the bonding roll 106 and the outer circumferential surface 114 of the anvil roll 110 move at the same speeds or different speeds.

During the bonding operation, the bonding roll 106 may rotate in a first direction 128 around the axis of rotation 108, and the anvil roll 110 may rotate in a second direction 130, opposite the first direction 128, around the axis of rotation 112 of the anvil roll 110. For example, a first substrate 102 and second substrate 104 may advance in a machine direction MD between the bonding roll 106 and the anvil roll 110. More specifically, the first substrate 102 includes a first surface 132 and a second surface 134 opposite the first surface 132, and the second substrate 104 includes a first surface 136 and a second surface 138 opposite the first surface 136. As such, the first surface 132 of the first substrate 102 is contacted by the bonding roll 106, and the second surface 138 of the second substrate 104 is contacted by the anvil roll 110. The second surface 134 of the first substrate 102 and the first surface 136 of the second substrate 104 contact each other. It is to be appreciated that any portion of the first substrate 102 and the second substrate 104 may overlap forming an overlap portion. For example, as illustrated in FIG. 1B, the first substrate 102 overlaps a portion of the second substrate 104. As the first substrate 102 and the second substrate 104 advance through the nip 126, which is formed by the bonding surface of the one or more pressure applying members 116 and the anvil roll 110, the one or more pressure applying members 116 contact the first substrate 102 and compresses the first substrate 102 and second substrate 104 between the bonding surface of the pressure applying member 116 and the anvil roll 110. In turn, the pressure generated at the nip causes the first and second substrate material to yield. The bonding surface presses the yielded substrate material 140 of at least one of the first and second substrates 102, 104 together to form a discrete bond region 142 between the first and second substrates 102, 104.

Thus, the apparatus 100 may form a laminate 105 including first and second substrates 102, 104 bonded together by discrete bond regions 142, without the use of adhesives. It is to be appreciated, however, that the bonding apparatus 100 may also be used in combination with adhesives. Although FIG. 1A illustrates the apparatus 100 bonding two substrates together, it is to be appreciated that the apparatus may bond more than two substrates together. In addition, it is to be appreciated that the apparatus may also be used to consolidate a single substrate, such as to bond fibers of a nonwoven together.

It is to be appreciated that the bonding apparatus 100 may also be configured in various ways. For example, different types of motor arrangements may be used to rotate the bonding roll 106 and anvil roll 110. For example, the bonding roll 106 and the anvil roll 110 may be driven independently with two independent motors. Or, a motor may be used to directly drive the bonding roll via pulley and belt drive the anvil roll. Or, when bearer rings are used, only one of the rolls may be driven, and the other roll is driven by the contact surfaces of the bearer rings. In addition, the nip pressure between the bonding surface and the anvil roll may be generated in various ways. In some embodiments, the bonding apparatus 100 is configured to include a nip pressure above 20,000 PSI between the bonding surface 160 and the anvil roll 110. In some embodiments, the bonding apparatus 100 is configured to define a nip pressure from about 20,000 PSI to about 120,000 PSI, or from about 60,000 PSI to about 70,000 PSI between the bonding surface 160 and the anvil roll 110. In some embodiments, the bonding apparatus 100 is configured to define a nip pressure of about 60,000 PSI between the bonding surface 160 and the anvil roll 110. The pressure at the nip may depend, in part, on the area of the bond pattern, the basis weight of the substrate, the modulus of the substrate, the type of substrate, and the speed at which the bonding is completed, for example.

In a rotary configuration, the bonding roll 106 and anvil roll 110 may be considered to have a machine direction MD as indicated in FIGS. 1A and 1B. The bonding roll and the anvil roll rotate counter to one another to provide for a direction of movement though the nip 126 in the machine direction MD.

The pressure applying members may be joined to the bonding roll or the pressure applying members and the bonding roll may be integrally formed.

As previously described, the bonding surface of the pressure applying member 116 operatively engages the outer circumferential surface 114 of the anvil roll 110 to bond one or more substrates. The bonding roll 106 may include one or more pressure applying members 116 extending radially away from the outer circumferential surface 118 of the bonding roll 106. Traditionally, the bonding roll 106 including one or more pressure applying members 116 is designed such that the pressure applying member height, the height from the bonding surface of the pressure applying member to the outer circumferential surface 118 of the bonding roll, is the shortest possible height to achieve the desired bond. Further, the pressure applying members were designed for minimal compression or increased stiffness when the pressure applying member operatively engages the anvil roll 110. Due to the relatively short pressure applying member height and the minimal compression of the pressure applying member, operating parameters such as the distance between the bonding surface and the outer circumferential surface 114 of the anvil roll 110, the thickness of the substrates to be bonded, and the pressure that may be exerted on the substrate by the pressure applying member, must be maintained within relatively tight tolerances to prevent premature failure of the apparatus and/or defects in the substrate. More specifically, the substrates have a yield strength and an ultimate strength. The operative engagement of the pressure applying member and anvil roll should be such that the ultimate strength of the substrate is not exceeded during bonding. If the ultimate strength is exceeded during bonding, the substrate may tear or a hole may be created during the bonding process. A relatively stiff and short pressure applying member will reach both the yield strength and the ultimate strength of the material during bonding faster than a compliant pressure applying member.

A pressure applying member 116 having a pressure applying member height that may be relatively taller but has the ability to compress against the outer circumferential surface 114 of the anvil roll 112 may not exceed the yield strength of the substrate material as fast as a traditional pressure applying member. This allows for a greater tolerance in operating parameters because there is a larger range in which the pressure applying member may be compressed before the substrate is damaged, such as by tearing or creating holes, by exceeding the ultimate strength of the substrate. As previously described, the yield strength should be exceeded to generate a bond.

Figure 2:
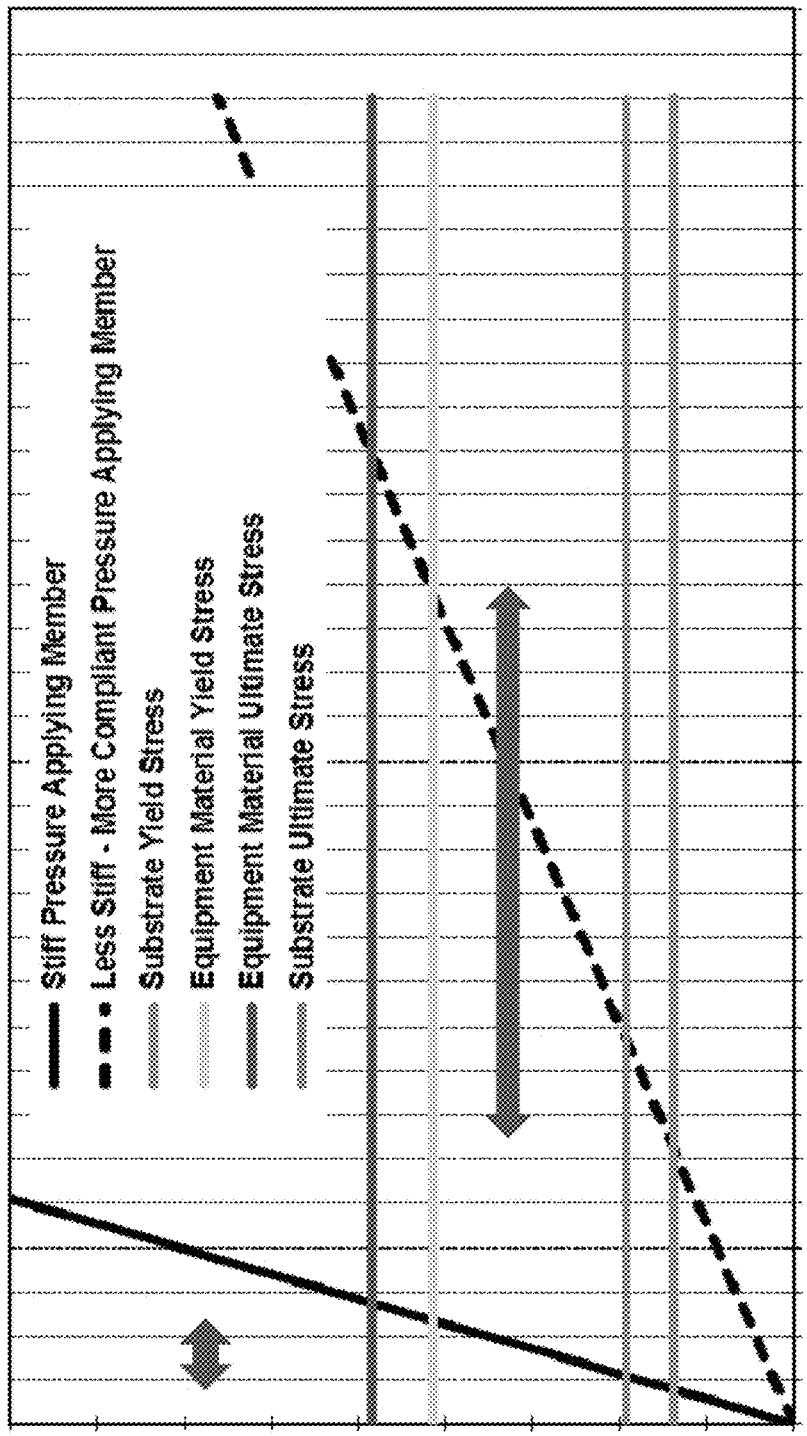
FIG. 2 is a chart of the bonding roll pressure applying member stress at various heights.

FIG. 2 illustrates an example of bonding using two different types of pressure applying members. As illustrated, the difference in reaching the yield strength and ultimate strength of a substrate with a relatively stiff pressure applying member is compared to a relatively compressible pressure applying member. As illustrated, the pressure applying member 116 that is compressible when operatively engaged by the anvil roll does not reach the ultimate strength of the substrate material as quickly as the more stiff pressure applying member. Thus, the compressibility allows for greater variance in operating parameters while still producing an effective bond because the pressure applying member is still capable of reaching the yield strength. Again, the pressure applying member with compressibility reached the yield strength while allowing for greater variance in operating parameters. It is also to be appreciated that the compressible pressure applying member also is less likely to adversely impact the equipment than a stiff pressure applying member. As illustrated, the stiff pressure applying member reaches the yield strength of the material of the equipment faster than the compliant pressure applying member. Thus, having a compliant pressure applying member may cause relatively less adverse impact on the equipment, such as the anvil roll and the pressure applying member itself. This may lead to prolonged operating life of the equipment, such as the anvil roll and the pressure applying member, and the ability to use a more diverse range of materials for the equipment.

FIGS. 3A-3E, 4A-4B, and 5A-5B illustrate examples of pressure applying member 116 geometries. A pressure applying member 116 may be generally cylindrical and include a bonding surface 160, a base surface 120 opposite the bonding surface, and a spring element 162 between the bonding surface 160 and the base surface 120. The base surface 120 may be the same surface as the outer circumferential surface 118 of the bonding roll 106 or a different surface from which each spring element 162 protrudes radially outward.

Each pressure applying member includes a pressure applying member height Hn between the bonding surface 160 and the base surface 120. The pressure applying member height may be from about 0.5 mm to about 4 mm, or from about 1 mm to about 3 mm, or from about 1.5 mm to about 2 mm, including all 0.1 mm increments within the specified ranges and all ranges formed therein or thereby. The pressure applying member height may be based, in part, on the substrate material, such as the basis weight and compressive modulus, in combination with the tooling modulus and the desired spring rate. In some embodiments, the pressure applying member height may be greater than the sum of the thicknesses of each of the substrates 102, 104 being bonded. The pressure applying members may be configured with the same or different heights. For example, the bonding roll 106 may include a plurality of pressure applying members and each of the plurality of pressure applying members may have the same or different heights.

The bonding surface 160 may include a bonding surface area. The bonding surface may be any shape such that the desired bond pattern is formed in the substrate. For example, the pressure applying members may have a perimeter that defines an elliptical shape. As such, in some embodiments, an elliptically shaped pressure applying member may have a bonding surface including a major axis and a minor axis that is less than the major axis. In some instances, the bonding surface may be configured such that the resulting bond regions also offer aesthetic benefits such as, for example, a stitched-like appearance along with a relatively smooth texture feel to the skin. The bonding surface may be changed based on the desired appearance of the bond on the substrate.

It is to be appreciated that various pressure applying member geometries may be used with the bonding apparatuses and processes herein. The pressure applying member may be any shape or pattern desired to be imparted to the substrate. For example, the pressure applying members may be round, oval, ellipse, polygonal, rectangular or bar-shaped, flower-shaped, or bow-shaped. It is also to be appreciated that the pressure applying members may form a logo and, thus, include a number of different shapes and/or letters. Various quantities of pressure applying members may be arranged in groupings, or patterns, to form discrete bonds.

The pressure applying member 116 may also include a spring element 162 positioned between the bonding surface 160 and the base surface 120. The spring element may include a proximal end portion 164 and a distal end portion 166, opposite the proximal end portion. The proximal end portion 164 may be joined to a portion of the bonding surface 160 and the distal end portion 166 may be joined to a portion of the base surface 120. The spring elements 162 may be positioned in a reduced stiffness zone 150. This is the zone between the bonding surface and the base surface. The reduced stiffness zone 150 may include one or more spring elements 162. The reduced stiffness zone 150 provides the pressure applying member 116 with increased flexure without exceeding the strength of the constituent material of the pressure applying member 116. The pressure applying member 116 may be provided with the desired flexure by not exceeding the fatigue strength of the constituent material of the pressure applying member 116, thereby providing improved fatigue resistance as compared to a conventional pressure applying member 116. Optionally, the reduced stiffness zone 150 of the pressure applying member 116 may be designed such that ultimate strength of the constituent material of the pressure applying member 116 is not exceeded. Further, the reduced stiffness zone 150 of the pressure applying member 116 may be designed such that when interacting with the anvil roll and compressing the substrate, the pressure applying member 116 does not reach the ultimate strength of the substrate material.

In some embodiments, the spring element 162 may be substantially perpendicular to base surface 120. The spring element 162 may also be at a spring angle α with respect to the base surface. The spring angle α may be from about 20 degrees to about 95 degrees and/or from about 65 degrees to about 90 degrees and/or from about 75 degrees to about 85 degrees, including all 0.1 degree increments within the specified ranges and all ranges formed therein or thereby. The spring element may be substantially straight (non-tapered). It is to be appreciated that each spring element may be positioned at a different spring angle or the same spring angle. In some embodiments, the pressure applying member 116 may comprise a curvilinear portion, or root radius 122, as illustrated in FIGS. 3D and 3E for example, located at the distal end portion 166 of the spring element 162 and adjacent the base surface 120. The root radius 122 may be from about 0.1 mm to about 0.5 mm or from about 0.2 mm to about 2 mm, including all 0.1 mm increments within the specified ranges and all ranges formed therein or thereby. Accordingly, the spring element 162 may not form a sharp angle with the base surface 120.

As illustrated in FIGS. 3A and 3B, the spring element 162 may include an outer circumferential surface 168 and an inner circumferential surface 170, opposite the outer circumferential surface 168. The inner circumferential surface 170 defines a void 172. This void 172 allows for the pressure applying member 116 to have a relatively greater compressibility during the bonding process. Stated another way, the configurations of the spring element 162 allows for the pressure applying member 116 to be less stiff, and thus, compress in the Z-direction during operative engagement with the anvil roll 110.

Figure 4A:
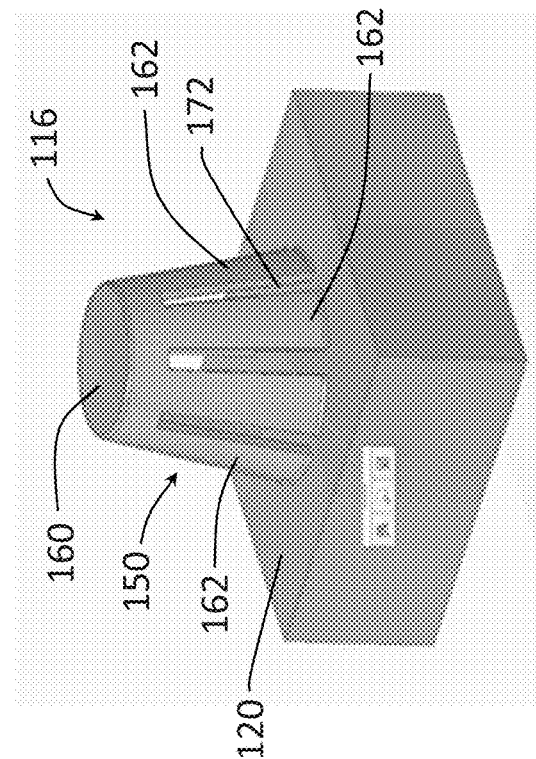
FIG. 4A is a perspective view of a pressure applying member.
Figure 4B:
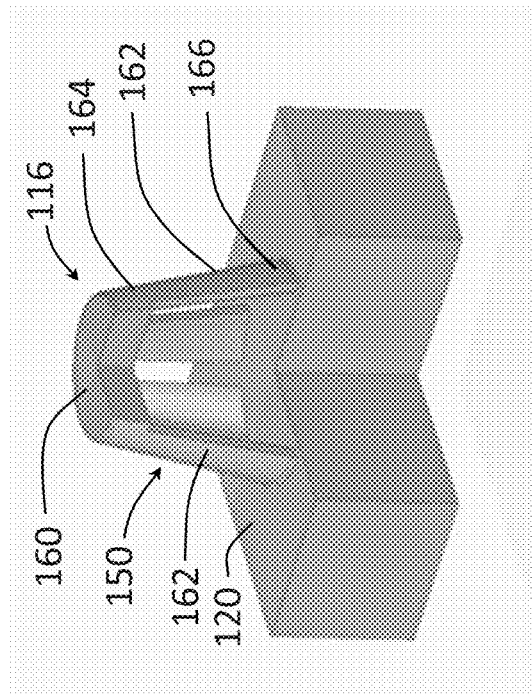
FIG. 4B is a perspective view of a pressure applying member including a cut-out portion.
Figure 5A:
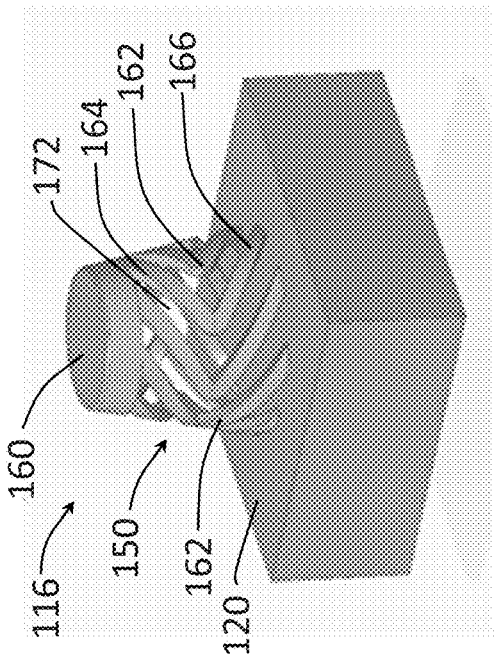
FIG. 5A is a perspective view of a pressure applying member.
Figure 5B:
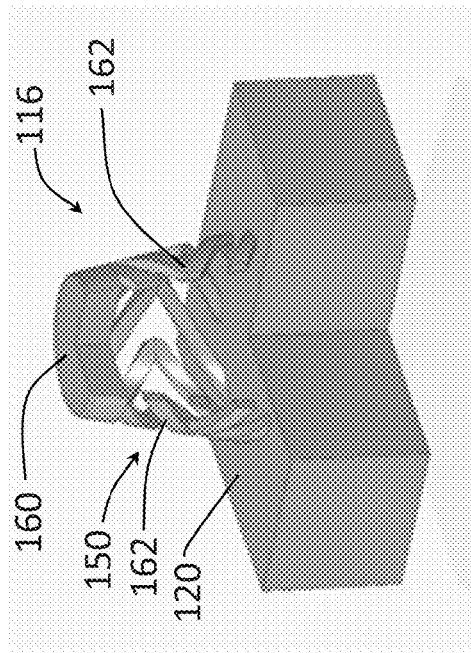
FIG. 5B is a perspective view of a pressure applying member including a cut-out portion.

FIGS. 4A-4B and 5A-5B illustrate a pressure applying member 116 including a plurality of spring elements 162. Each of the spring elements 162 may include a proximal end portion 164 joined to the bonding surface 160 and a distal end portion 166, opposite the proximal end portion, joined to the base surface 120. There may be voids 172, lack of material, between adjacent spring elements 162, as illustrated in FIGS. 4A and 5A. Further, the spring elements 162 may be a variety of shapes such as, for example, linear and curvilinear. The shape of the spring element 162 may be specific to the amount of compressibility in the pressure applying member 116 and/or the force that the pressure applying member 116 may withstand while being operatively engaged by the anvil roll 110.

It is to be appreciated that each spring element 162 of the plurality of spring elements may be a linear spring (i.e., obeys Hooke's law) or a non-linear spring, (i.e., does not obey Hooke's law). One of skill in the art will appreciate that a linear spring utilized for a spring element 162 of the plurality of spring elements is understood to mean that as long as each spring element 162 is not stretched or compressed beyond their elastic limit, each spring element 162 of will obey Hooke's law, which states that the force with which the spring element 162 pushes back is linearly proportional to the distance from its equilibrium length such that:

$$\sigma = E\epsilon$$

where:
$\sigma$=Stress;
E=Modulus of Elasticity; and,
$\epsilon$=Axial Unitary Deformation.
The above equation may be re-written as:

$$F = -kx$$

where:
F=resulting force vector (i.e., the magnitude and direction of the restoring force the spring exerts);
k=spring constant (e.g., also the force constant, or stiffness, of the spring). This is a constant that depends on the spring's material, shape, and/or construction. The negative sign indicates the force exerted by the spring is in the direction opposite its displacement; and,
x=displacement vector (i.e., the distance and direction the spring is deformed from its equilibrium length).

According to this formula, a graph of the applied force F as a function of the displacement x will be a straight line passing through the origin, whose slope is k. In other words, the spring constant is a characteristic of a spring which is defined as the ratio of the force affecting the spring to the displacement caused by it. By way of example, springs suitable for use as a spring element 162 may include coil springs and other common springs that obey Hooke's law. Springs suitable for use as a spring element 162 may be based on simple beam bending that may produce forces that vary non-linearly with displacement. Further, if made with constant pitch (wire thickness), conical springs may have a variable rate. However, a conical spring suitable for use as a spring element 162 may be made to have a constant rate by creating the spring with a variable pitch. A larger pitch in the larger-diameter coils and a smaller pitch in the smaller-diameter coils will force the spring to collapse or extend all the coils at the same rate when deformed.

Since force is equal to mass, m, times acceleration, a, the force equation for a spring obeying Hooke's law provides:

$$F=ma \rightarrow -kx=ma$$

It may be preferred that the mass of the spring element 162 be small in comparison to the mass of the bonding surface 160. Since acceleration is simply the second derivative of x with respect to time, $$-kx = m\frac{d^2 x}{dt^2}$$

This is a second order linear differential equation for the displacement as a function of time. Re-arranging:

$$\frac{d^2 x}{dt^2} + \frac{k}{m}x = 0$$

the solution of which is the sum of a sine and cosine:

$$x(t) = A\sin\left(t\sqrt{\frac{k}{m}}\right) + B\cos\left(t\sqrt{\frac{k}{m}}\right)$$

where:
A, B=arbitrary constants that may be found by considering the initial displacement and velocity of the mass.

As would be understood by one of skill in the art, a spring element may be seen as a device that stores potential energy, specifically elastic potential energy, by straining the bonds between the atoms of an elastic material. Hooke's law of elasticity states that the extension of an elastic rod (e.g., its distended length minus its relaxed length) is linearly proportional to its tension, the force used to stretch it. Similarly, the contraction (i.e., negative extension) is proportional to the compression (i.e., negative tension).

Hooke's law is a mathematical consequence of the fact that the potential energy of the rod is a minimum when it has its relaxed length. Any smooth function of one variable approximates a quadratic function when examined near enough to its minimum point as may be seen by examining the Taylor series. Therefore, the force—which is the derivative of energy with respect to displacement—will approximate a linear function. The force of a fully compressed spring is provided as:

$$F_{max} = \frac{Ed^4(L-nd)}{16(1+v)(D-d)^3 n}$$

where:
E=Young's modulus;
d=spring wire diameter;
L=free length of spring;
n=number of active windings;
v=Poisson ratio; and,
D=spring outer diameter.

One of skill in the art will appreciate that a non-linear spring utilized for a spring element 162 is understood to mean that a non-linear relationship exists between the force applied to the spring element and the spring element's resulting displacement. One of skill in the art will appreciate that a graph showing force vs. displacement for a non-linear spring element will be more complicated than a straight line, with a changing slope. Stated differently, a non-linear spring element does not obey Hooke's law such that the applied force is related to the relative displacement such that:

$$F=kF(x)$$

where:
F=applied force;
x=spring displacement from the spring's neutral position; and,
k=spring constant (i.e., stiffness).

The resulting spring constant is provided as:

$$k = \frac{dF}{dx}$$

Therefore, it should be understood and appreciated by one of skill in the art that a spring element 162 suitable for use in the pressure applying member 116 may include all springs, no matter the design or shape, that obey, or do not obey, Hooke's law. Further, it may be understood and appreciated by one of skill in the art that spring elements 162 comprising any combination of linear and non-linear springs may be suitable for use in the pressure applying member 116. In other words, any suitable combination of spring elements may include all springs, no matter the design, matter of construction, or shape that obey, or do not obey, Hooke's law that are suitable for use in the pressure applying member 116 in order to provide the desired degree of localized deformation.

Each spring element 162 of the plurality of spring elements may be provided with the same spring constant, k. Alternatively, it is believed that each spring element 162 of the plurality of spring elements may be provided with an individual spring constant, k. In other words, a first spring element of the plurality of spring elements may be provided with a first spring constant, $k_1$, and a second spring element of the plurality of spring elements may be provided with a second spring constant, $k_2$. The first spring constant, $k_1$, may be different from the second spring constant, $k_2$ (e.g., the first spring constant, $k_1$, may be less than the second spring constant, $k_2$, or the first spring constant, $k_1$, may be greater than the second spring constant, $k_2$). By way of benefit of the pressure applying member 116, each spring element of the plurality of spring elements may provide the pressure applying member 116 with the ability to have a localized, discrete, flexural modulus thereby increasing the operable lifetime and reducing potential catastrophic degradation.

In mechanics, the flexural modulus or bending modulus, E, is an intensive property that is computed as the ratio of stress to strain in flexural deformation, or the tendency for a material to bend. It is determined from the slope of a stress-strain curve produced by a flexural test (such as ASTM D790), and has units of force per area.

For a 3-point test of a rectangular beam behaving as an isotropic linear material, where w and h are the width and height of the beam, I is the second moment of area of the beam's cross-section, L is the distance between the two outer supports, and d is the deflection due to the load F applied at the middle of the beam, the flexural modulus, E, is provided by:

$$E_{bend} = \frac{L^3 F}{4wh^3 d}$$

From elastic beam theory, the deflection, d, is provided as:

$$d = \frac{L^3 F}{48IE}$$

For a rectangular beam, the moment, I, is provided by:

$$I = \frac{1}{12}wh^3$$

Thus:

$$E_{bend} = E \text{(i.e., Elastic modulus)}$$

One of skill in the art will recognize that ideally, flexural or bending modulus of elasticity is equivalent to the tensile or compressive modulus of elasticity. These values may be different, especially for plastic materials.

Figure 7:
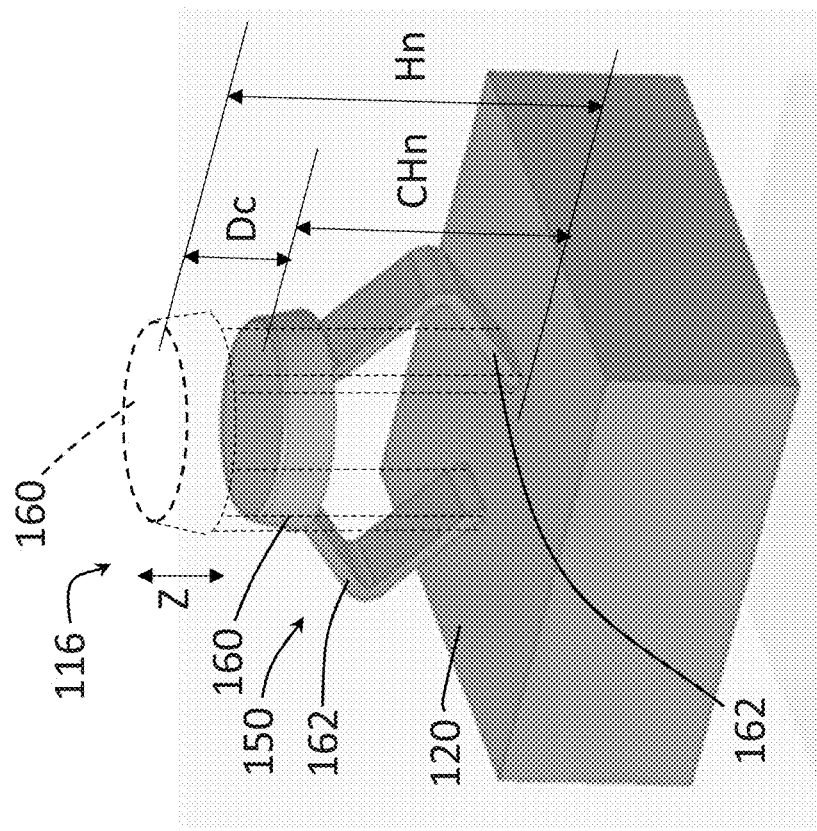
FIG. 7 is a perspective view of a pressure applying member.
Figure 6:
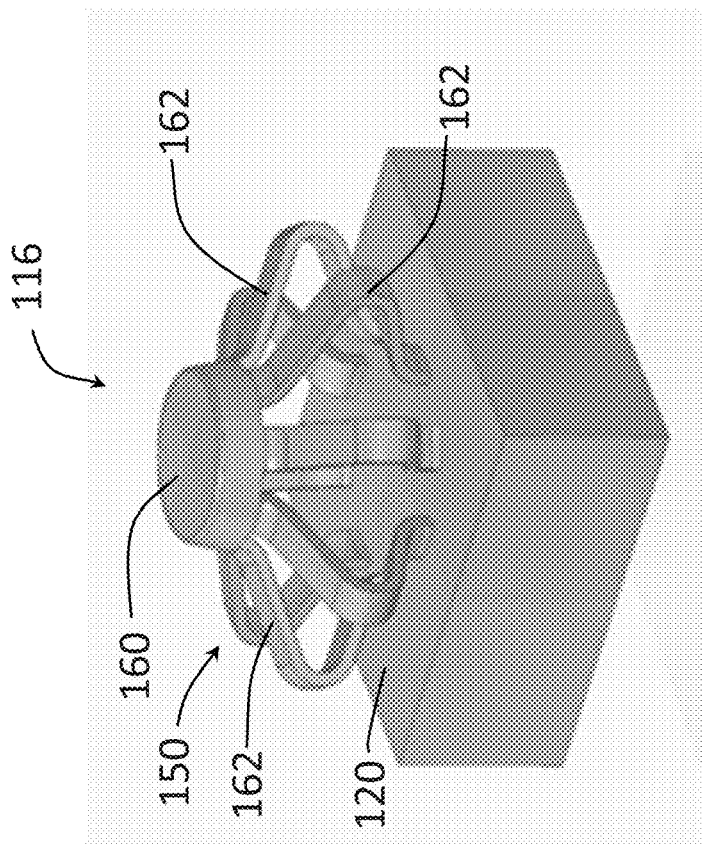
FIG. 6 is a perspective view of a pressure applying member.

Each spring element 162 of the plurality of spring elements may provide a discrete, and distinct flexural modulus for each portion of the pressure applying member 116. Each pressure applying member 116 may be compressed in the Z-direction by operative engagement with the anvil roll 110 uniformly or non-uniformly. For example, as illustrated in FIGS. 6 and 7, the spring elements 162 compress in the Z-direction when operatively engaged by the anvil roll 110. The amount of compression depends, in part, on the spring element and the force applied to the bonding surface 160 by the anvil roll 110. A plurality of spring elements may be used in a single pressure applying member 116, such as illustrated in FIG. 6. Each of the plurality of spring elements may include different properties such that the pressure applying member 116 reacts in a certain way when engaged by the anvil roll 110.

For example, the anvil roll 110 may operatively engage the pressure applying member 116 having a first group of spring elements including a first spring constant and a second group of spring elements including a second spring constant, which is different than the first spring constant. The spring elements having different spring constants may compress by various amounts in the Z-direction. More specifically, the anvil roll 110 may engage the pressure applying member 116 including the first group of spring elements having the first spring constant and this portion of the pressure applying member 116 may compress by a first compression distance. The anvil roll 110 may then engage the portion of the pressure applying members 116 including the second group of spring elements having the second spring constant causing the pressure applying member 116 to compress by a second compression distance. However, due to the differing spring constants of the spring elements, the first compression distance may be different than the second compression distance. It is to be appreciated that other characteristics of the spring elements may be affected to change the amount the pressure applying member 116 is compressed, also referred to herein as the compression distance, such as the height of the pressure applying member, the shape of the pressure applying member, and the material of the pressure applying member.

In some embodiments, the pressure applying member 116 may be configured to be compressed uniformly. FIG. 7 illustrates an example of the compression of a pressure applying member 116. As shown, the pressure applying member 116 is initially positioned at a pressure applying member height Hn. The pressure applying member height Hn is the position of the pressure applying member 116 prior to operative engagement with the anvil roll 110. For example, in some embodiments, the pressure applying member height Hn may be greater than about 0.5 mm. Once operatively engaged by the anvil roll 110, the pressure applying member 116 is compressed to a compressed pressure applying member height CHn. The difference between the pressure applying member height Hn and the compressed pressure applying member height CHn is the compression distance Dc. The compression distance Dc may be greater than about $1 \times 10^{-9}$ m or greater than about $1 \times 10^{-6}$ m or greater than about $1 \times 10^{-5}$ m or greater than about $1 \times 10^{-4}$ m. In some embodiments, the compression distance Dc may be from about $1 \times 10^{-6}$ m to about 1 mm, including all increments between the recited range. As previously discussed, the pressure applying member height and the ability of the pressure applying member to compress allows for greater flexibility in the operating parameters and minimizes the substrate being damaged during the bonding process.

In some embodiments, such as illustrated in FIGS. 8 and 9, the bonding roll 106 includes a plurality of pressure applying members 116. The pressure applying members 116 may be arranged in various patterns. Further, the pressure applying members 116 may have different characteristics, such as height, shape, material, and spring constants, such that the each of the plurality of pressure applying members 116 compresses individually and to varying degrees. For example, the bonding roll 106 may include a first pressure applying member and a second pressure applying member. The first pressure applying member may compress a first compression distance and the second pressure applying member may compress a second compression distance. The first compression distance may be different than the second compression distance. The ability for the pressure applying members to act independently allows for substrates having varying thickness to be bonded on a single roll. This also allows for a non-balanced pattern to be imparted to the substrate. As illustrated in FIG. 9, the pattern of pressure applying members may include various sizes and shapes, and these pressure applying members may be placed in various locations on the bonding roll. Traditionally, bonding patterns would need to be balanced such that equal force was exerted over the roll during the bonding process. This balanced force allowed for uniform bonding of the substrate. However, since the pressure applying members 116 may be designed with varying compression distances, the bonding pattern may account for the varying force while still imparting the desired bond pattern into the substrate.

It is also to be appreciated that groups of pressure applying members 116 positioned adjacent one another may have varying properties, such as spring constants, height, and material. For example, as illustrated in FIG. 8, the plurality of pressure applying members 116 may be separated into a first group of pressure applying members 174, a second group of pressure applying members 176, and a third group of pressure applying members 178. The first group of pressure applying members 174 may have a first spring constant and, thus, compress by a first compression distance. The second group of pressure applying members 176 may have a second spring constant and, thus, compress by a second compression distance. Similarly, the third group of pressure applying members 178 may have a third spring constant and, thus, compress by a third compression distance. The first spring constant may be different than the second spring constant and the third spring constant. The second spring constant may be different than the first spring constant and the third spring constant. It is also to be appreciated that the spring constant may be the same for any of the groups. For example, the first spring constant and the third spring constant may be the same. Further, the first compression distance may be different than the second compression distance and the third compression distance. It is also to be appreciated that the compression distance may be the same for any of the groups. For example, the first compression distance may be the same as the third compression distance. However, due to the ability of the individual pressure applying members to compress, any given pressure applying member may compress by a different amount. The difference in compressibility may also be due in part, for example, to varying thicknesses in the substrate or imperfections in the anvil roll.

The pressure applying member 116 may be manufactured in the form of a uni-body construction. Such uni-body constructions typically enable building parts one layer at a time through the use of typical techniques such as SLA/stereo lithography, SLM/Selective Laser Melting, RFP/Rapid freeze prototyping, SLS/Selective Laser sintering, EFAB/Electrochemical fabrication, DMDS/Direct Metal Laser Sintering, LENS/Laser Engineered Net Shaping, DPS/Direct Photo Shaping, DLP/Digital light processing, EBM/Electron beam machining, FDM/Fused deposition manufacturing, MJM/Multiphase jet modeling, LOM/Laminated Object manufacturing, DMD/Direct metal deposition, SGC/Solid ground curing, JFP/Jetted photo polymer, EBF/Electron Beam Fabrication, LMJP/liquid metal jet printing, MSDM/Mold shape deposition manufacturing, SALD/Selective area laser deposition, SDM/Shape deposition manufacturing, combinations thereof, and the like. However, as would be recognized by one familiar in the art, such a uni-body pressure applying member 116 may be constructed using these technologies by combining them with other techniques known to those of skill in the art such as casting.

Further, pressure applying member 116 may be manufactured from conventional machining techniques utilizing manually controlled devices, such as hand wheels or levers, or mechanically automated devices. The pressure applying member 116 may be manufactured from machining techniques utilizing Computer Numeric Control (CNC) automated machine tools operated by precisely programmed commands encoded on a storage medium (computer command module, usually located on the device). Such CNC systems may provide end-to-end component design using computer-aided design (CAD) and computer-aided manufacturing (CAM) programs. These programs produce a computer file that is interpreted to extract the commands needed to operate a particular machine by use of a post processor, and then loaded into the CNC machines for production. Since any particular component might require the use of a number of different tools—drills, saws, etc.—modern machines often combine multiple tools into a single "cell". In other installations, a number of different machines are used with an external controller and human or robotic operators that move the component from machine to machine. In either case, the series of steps needed to produce any part is highly automated and produces a part that closely matches the original CAD design.

In any regard, machine motion is controlled along multiple axes, normally at least two (X and Y), and a tool spindle that moves in the Z (depth). The position of the tool is driven by direct-drive stepper motor or servo motors in order to provide highly accurate movements, or in older designs, motors through a series of step down gears. Open-loop control works as long as the forces are kept small enough and speeds are not too great. On commercial metalworking machines, closed loop controls are standard and required in order to provide the accuracy, speed, and repeatability demanded. CNC may include laser cutting, welding, friction stir welding, ultrasonic welding, flame and plasma cutting, bending, spinning, hole-punching, pinning, gluing, fabric cutting, sewing, tape and fiber placement, routing, picking and placing, and sawing.

Alternatively, pressure applying member 116 may be manufactured from multiple materials in order to utilize the unique physical characteristics of the material forming each part of the pressure applying member 116, such as the bonding surface 160, the spring elements 162, and the base surface 120. By way of non-limiting example, bonding surface 160 may be formed from a first material having a first set of material properties and the spring elements 162 may be formed from a second material having a second set of material properties. Alternatively, each spring element 162 of the plurality of spring elements may be formed from materials having differing material properties in order to provide a differential flexural modulus to a respective portion of the pressure applying member 116. Each pressure applying member 116 may include a spring element 162 formed from differing materials such that each pressure applying member 116 may be compressed to an individual compression distance.

In some embodiments, each portion of the pressure applying member 116 may be fabricated separately and combined to form the pressure applying member 116. This may facilitate assembly and repair work to the parts of the pressure applying member 116 such as coating, machining, heating and the like, etc. In such techniques, two or more of the components of the pressure applying member 116 commensurate in scope with the instant disclosure may be combined into a single integrated part.

One of skill in the art may model the particular pressure applying member shapes, spring shapes, physical design elements, material characteristics, and the like to provide the desired characteristics of the pressure applying member and spring elements using numerous modeling techniques including, but not limited to, finite element analysis (FEA). Such an analysis tool may be used to provide for virtually any design of pressure applying members necessary for the substrate bonding operation envisioned by the present disclosure. This analysis may also be used for the design and configuration of the bonding roll including a plurality of pressure applying members and the bonding rolls operative engagement with the anvil roll.

It is also to be appreciated that the spring elements 162 may be arranged as pairs of spring elements. Each spring element of a pair of spring elements may be joined at a proximal end to the boding surface 160 and a distal end of each spring element of a pair of spring elements may be joined to the base surface 120. In this arrangement, a first spring element of a pair of spring elements may deflect in a first direction in a first combination of the MD, CD, and/or Z-directions relative to the base surface 120 and a second spring element of a pair of spring elements may deflect in a second direction in a second combination of the MD, CD, and/or Z-directions relative to the base surface 120. This may acceptably accommodate any torsional forces applied to and experienced by pressure applying member 116 relative to the base surface 120 when the pressure applying member 116 is operatively engaged with an opposed anvil roll.

Stated another way, it is to be appreciated that providing the plurality of spring elements as arranged pairs of spring elements may facilitate the deflection of the pressure applying member 116 into any desired combination of the MD, CD, and/or Z-directions. Since the pressure applying member 116 is designed to be disposed in contacting engagement with an opposed anvil roll in rotary fashion with a substrate disposed therebetween, one of skill in the art will likely appreciate that the forces disposed upon the bonding roll by an opposed anvil roll and any substrate disposed therebetween may not be solely limited to forces in the Z-direction. Therefore, providing each pressure applying member 116 with the possibility for three-dimensional movement due to the individual flexion provided by each spring element of a given pair of spring elements may reduce any wear caused by repeated out-of-plane deformation of the pressure applying member 116 that may result in rapid degradation of the bonding surface 160.

It is to be appreciated that the spring elements may be defined by not only a void area but an area of less material, such as where the pressure applying member has been thinned or a portion of the material removed. A void may be provided by machining out constituent material from the pressure applying member to leave a void in the pressure applying member. Optionally, additive manufacturing may be used to build up the pressure applying member and not deposit material or not deposit as much material at a position in which a void or reduced stiffness area is desired. Examples of voids and reduced stiffness zones for a knife may be found in U.S. application Ser. No. 15/371,596 filed on Dec. 7, 2016 and U.S. application Ser. No. 15/446,378 filed on Mar. 1, 2017.

The pressure applying member 116 may also include a shoulder such as disclosed in U.S. Pat. Publication No. 2015/0173961. Pressure applying members with significant shoulders, or edge breaks, have been proven to improve bond strength and reduce the tendency of a substrate, e.g., a topsheet, to peel. It is believed that the improved pressure applying members create stronger bonds in part due to less torn fibers/filaments next to the bond sites. The reduced shearing or tearing of fibers is believed to be the cause of improved bond strength.

Figure 10:
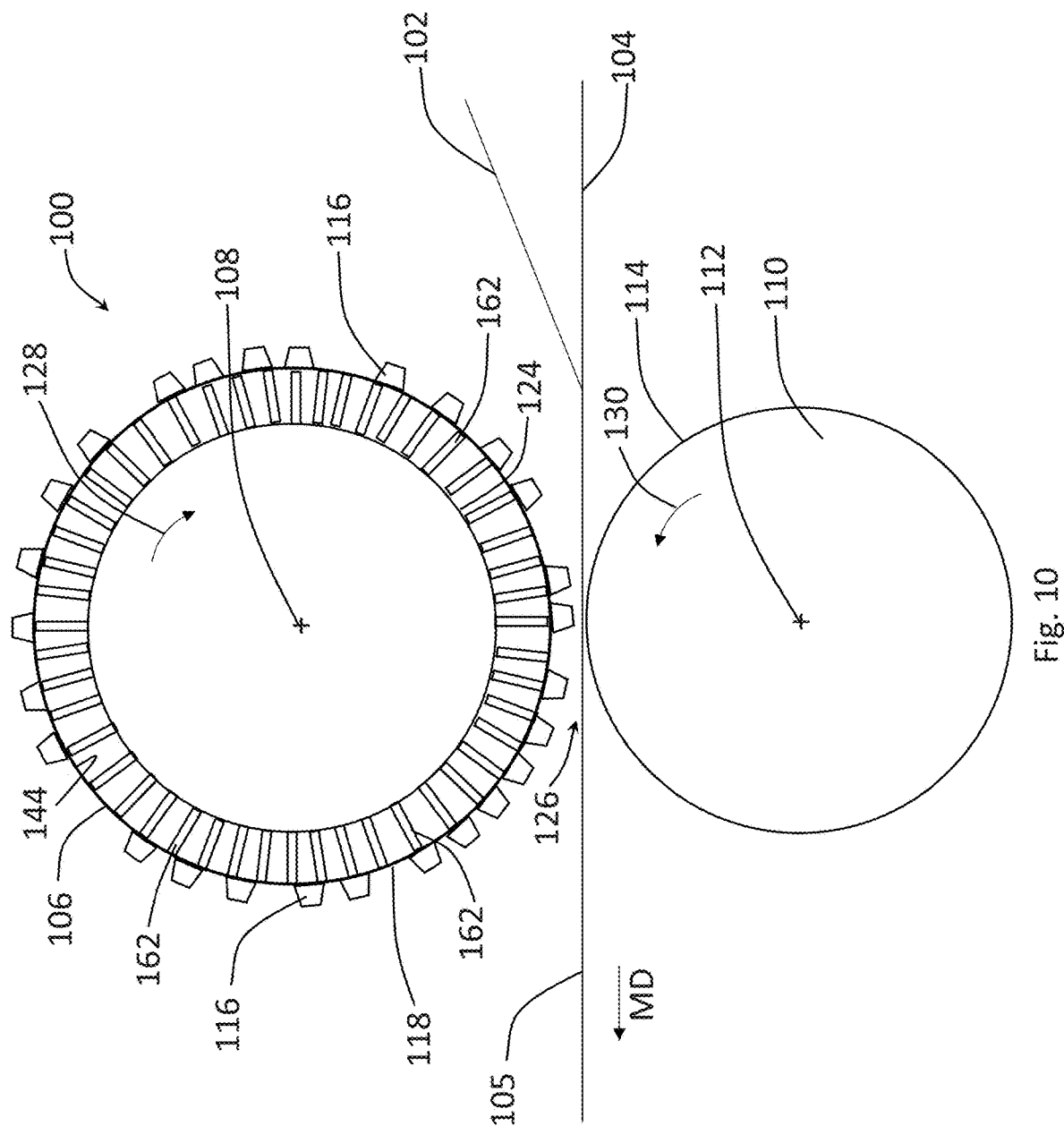
FIG. 10 is a side view of a bonding apparatus.

In some embodiments, referring to FIG. 10, the bonding roll 106 may include an outer circumferential surface 118 and an inner circumferential surface 124. The outer circumferential surface 118 is positioned radially outward from the inner circumferential surface 124. The bonding roll 106 may also include a first bonding surface 144, which is opposite to the outer circumferential surface 118 and in facing relationship with the inner circumferential surface 124. The bonding roll 106 may include a plurality of pressure applying members 116 joined to the outer circumferential surface 118, such as previously described. The bonding roll 106 may also include a plurality of spring elements 162, such as previously described. The plurality of spring element 162 may be positioned between the first bonding surface 144 and the inner circumferential surface 124. More specifically, the proximal end portion of the spring element may be joined to the first bonding surface 144 and the distal end portion of the spring element may be joined to the inner circumferential surface 124. In some embodiments, the individual pressure applying members 116 may not include the spring element and the spring elements present in the bonding roll 106 act to provide the desired compressibility during the bonding process. In some embodiments, the individual pressure applying members 116 include a spring element and the bonding roll includes additional spring elements to provide the desired compressibility during the bonding process. It is to be appreciated that the spring constant of each of the plurality of spring elements may be the same or different, such as previously disclosed.

As illustrated in FIG. 11, in some embodiments, two bonding rolls may be used to bond the substrate. More specifically, a first bonding roll 106 including a first plurality of bonding pressure applying members having spring elements may operatively engage a second bonding roll 146 including a second plurality of bonding pressure applying members having spring elements. The first bonding roll 106 may be aligned with the second bonding roll 146 such that the first plurality of pressure applying members operatively engage the second plurality of pressure applying members to bond the substrate as the substrate traverses in the machine direction MD.

Figure 12B:
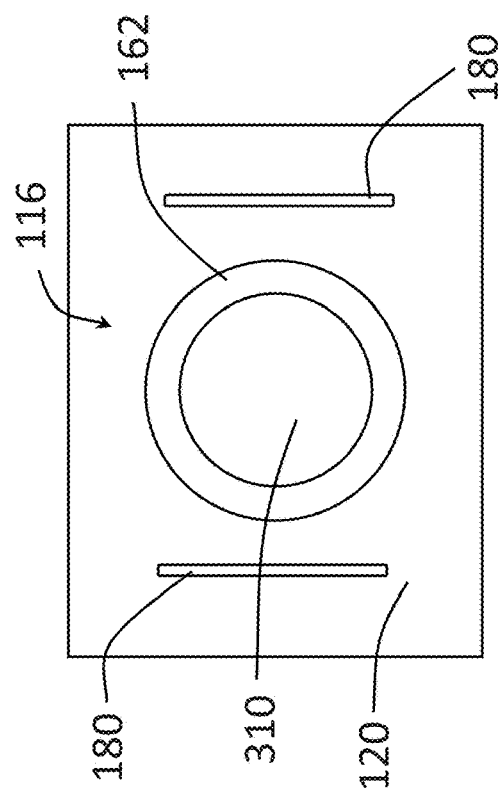
FIG. 12B is a top view of a pressure applying member.
Figure 12A:
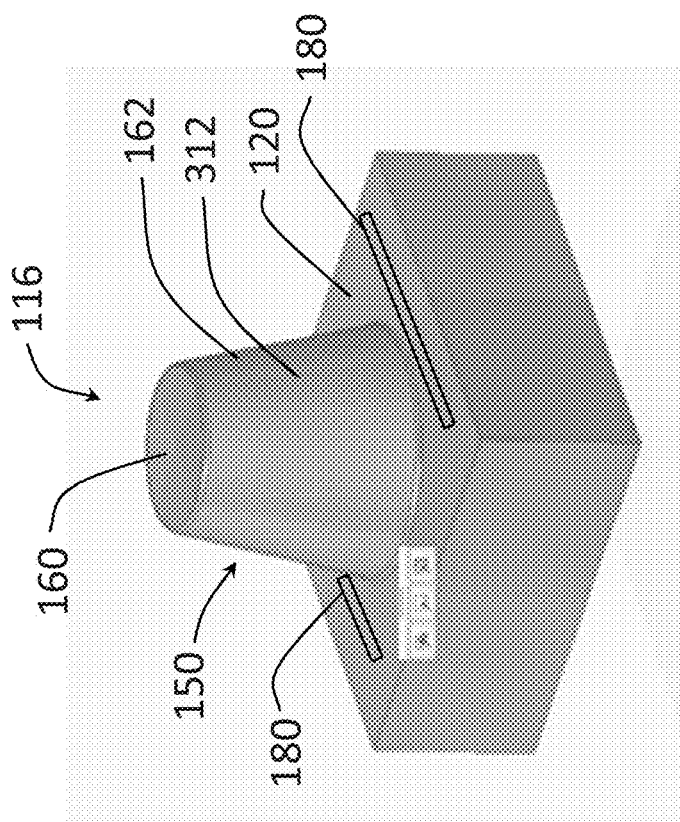
FIG. 12A is a perspective view of a pressure applying member.

It is also to be appreciated that additional compressibility or compressibility may be added to the base surface 120 of the pressure applying member 116, such as illustrated in FIGS. 12A and 12B. For example, the base surface 120 may include void areas or areas of reduced material thickness 180. The void areas or reduced material thickness areas 180 may be any shape such that compressibility is added to the pressure applying member.

In summary, a method for forming a bond includes the following steps. A bonding roll may be rotated about an axis of rotation. The bonding roll may include a first pressure applying member extending radially outward from the forming roll. The first pressure applying member may include a first spring element. An anvil roll may be positioned adjacent the bonding roll and may rotate about an axis of rotation. The anvil roll and the bonding roll are positioned with respect to one another such that a nip is formed between the anvil roll and the bonding roll. A first substrate and a second substrate are advanced in the machine direction. The first substrate and the second substrate may form an overlap portion. The first and second substrates are advanced through the nip in the machine direction. The bonding roll and the anvil roll rotate as the substrates are passed through the nip causing the bonding roll and the anvil roll to operatively engage. More specifically, as the bonding roll and the anvil roll rotate, the first pressure applying member compresses at least a portion of the overlap portion forming a bond. It is to be appreciated that the pressure applying member may engage a portion of the substrates other than the overlap portion and a single substrate may be advanced through the nip. It is also to be appreciated that a single substrate may be folded and the folded portion may be advanced through the nip. As the first pressure applying member engages the substrate and the anvil roll, the first pressure applying member may be compressed by a first compression distance. The first compression distance may be greater than about $1 \times 10^{-9}$ m.

The bonding roll may include any number of pressure applying members such that the desired bonds are imparted to the substrate. For example, the bonding roll may include a second pressure applying member having a second spring element. Further, the first spring element of the first pressure applying member includes a first spring constant and the second spring element of the second pressure applying member includes a second spring constant. The first spring constant and the second spring constant may be different or the same. It is also to be appreciated that each of the first pressure applying member and the second pressure applying member may produce forces that vary non-linearly with displacement. The second pressure applying member may be compressed by a second compression distance. The first compression distance may be different than the second compression distance.

The substrate passes through the nip including one or more bonds. The substrate may continue to advance in the machine direction to downstream processes.

Figure 13:
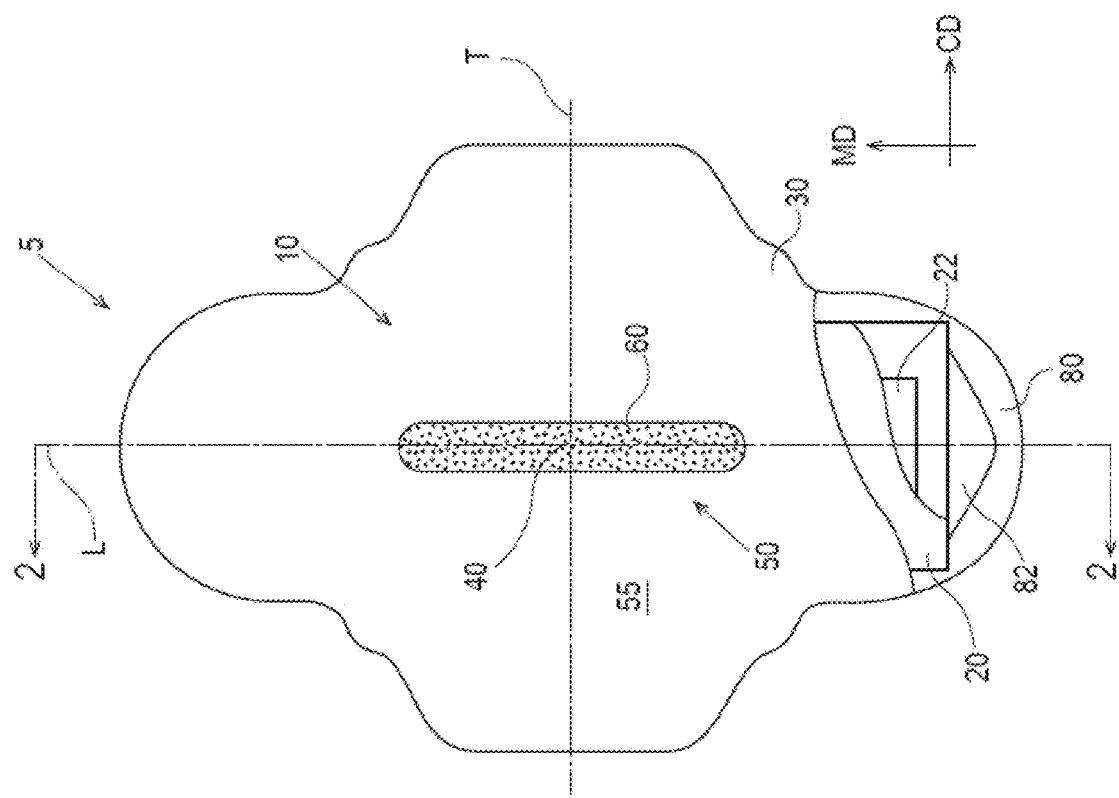
FIG. 13 is a top view of an absorbent article.
Figure 14:
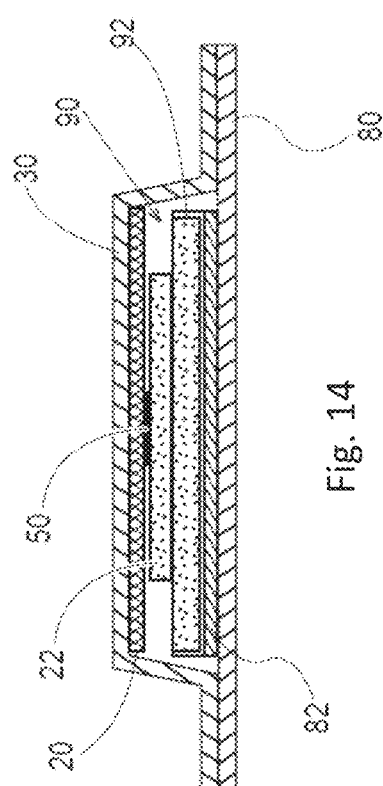
FIG. 14 is a cross-sectional view of the absorbent article taken about line 2-2 of FIG. 13.
Figure 15:
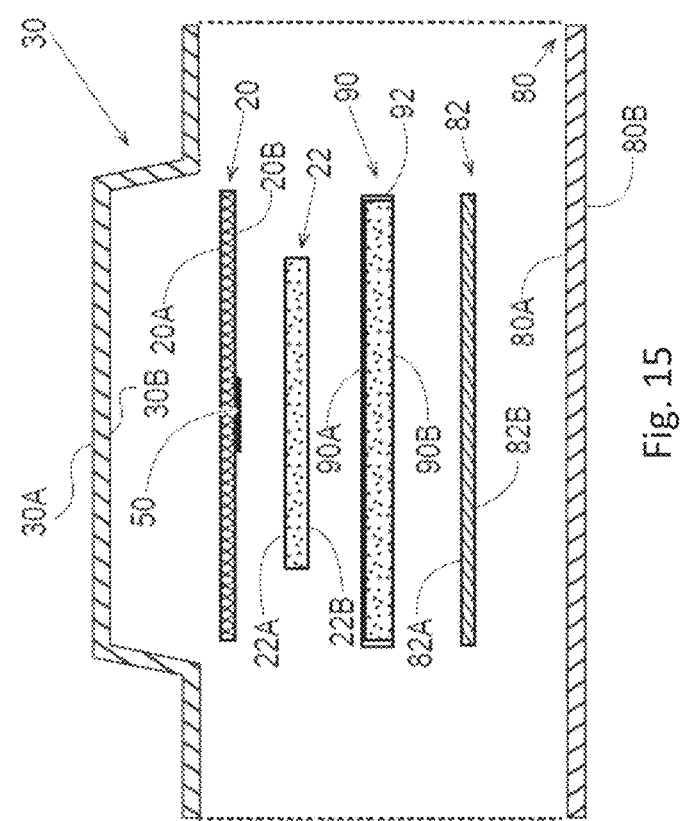
FIG. 15 is an exploded view of the absorbent article cross section of FIG. 14.

An example absorbent article 5 according to the present disclosure, shown in the form of a sanitary napkin or incontinence pad, is represented in FIGS. 13-15. This type of absorbent article is shown for illustration purpose only as the present disclosure can be used for making a wide variety of other absorbent articles. FIG. 13 is a top view of the example absorbent article 5, in a flat-out state, with portions of the structure being cut-away to more clearly show the construction of the absorbent article 5. FIG. 14 is a cross-sectional view of the absorbent article of FIG. 13 taken along line 2-2, while FIG. 15 is an exploded cross-sectional view of the absorbent article of FIG. 14.

Referring to FIG. 13, the absorbent article 5 can have a substantially planar configuration and a centroid 40. The centroid 40 is the in-plane center of mass of the absorbent article 5. The centroid 40 is at the intersection between the longitudinal centerline L and transverse centerline T. The transverse centerline T is orthogonal to the longitudinal centerline L. The absorbent article 5 can, but need not be, symmetric about the transverse centerline T. The absorbent article 5 has a body-facing surface 10 and a garment facing surface (not shown).

The absorbent article 5 comprises a plurality of layers to promote certain liquid handling behaviors. Example layers include a liquid-permeable topsheet 30 and an absorbent core 90. Some embodiments can also include a top core 22, as illustrated. The absorbent core 90 can have a number of suitable arrangements, for example the absorbent core 90 can have a tissue outer wrapping 92 (FIG. 15). The absorbent articles can also have a backing material 82 and a backsheet 80.

To help ensure that fluids flow into the absorbent core 90, some absorbent articles are constructed with what is sometimes referred to as a secondary topsheet 20 ("STS") positioned intermediate the topsheet 30 and the absorbent core 90. This secondary topsheet 20 is designed to acquire the fluid on the liquid-permeable topsheet 30 and distribute it to the underlying absorbent core 90. To help ensure that the secondary topsheet 20 transfers the fluid to the absorbent core 90, the secondary topsheet 20 can have sufficient capillarity to draw the fluid through the liquid-permeable topsheet 30. To ensure that the fluid flow continues onto the absorbent core 90, the secondary topsheet 20 can be designed with more permeability than the absorbent core 90, and less capillarity than the absorbent core 90. For example, a secondary topsheet can be an airlaid-tissue web made from hydrophilic cellulosic fibers and polyethylene powder, sometimes referred to as an airlaid STS. Or, a secondary topsheet can be a spunlace web. A spunlace web may be a hydroentangled fibrous structure with a basis weight between about 35 grams per square meter (gsm) and about 85 gsm. The spunlace web may comprise about 30% to about 60%, by weight, of cellulosic fibers, about 5% to about 30%, by weight, of non-cellulosic fibers, and about 30% to about 55%, by weight, of polyolefin-based binder fibers. Referring back to FIGS. 13 and 14, in one embodiment, the first substrate 102 comprises a secondary topsheet and the second substrate 104 comprises a topsheet. For example, the first substrate 102 may comprise a spunlace STS and the second substrate 104 may comprise a film-nonwoven composite topsheet, such as a polyethylene film-polyethylene nonwoven composite topsheet.

It is to be appreciated that the apparatuses and methods herein can be used to bond various types of substrates together. The substrates may comprise materials that can be deformed beyond their yield point by the compression in the nip of the apparatus. For example, in some embodiments the apparatus may be used to bond nonwoven substrates, such as for example, polypropylene nonwoven, polyethylene film, bi-component nonwoven or film, polyethylene terephthalate nonwoven or film. In some embodiments, the apparatuses and methods herein may be used to bond a substrate which includes a mixture of cellulosic fibers and polyethylene or polyethylene-polypropylene bicomponent fibers or particulate. In some embodiments, the substrates may have a basis weight of about 6 gsm to about 100 gsm. Other types of substrates can be sandwiched in between two layers of nonwovens or films.

The substrates may comprise any suitable woven, nonwoven, film, combination or laminate of any of the foregoing materials. Non-limiting examples of suitable substrates include cellulose, films, such as polymeric or thermoplastic films, foils, such as metallic foils (e.g. aluminum, brass, copper, and the like), webs comprising sustainable polymers, foams, fibrous nonwoven webs comprising synthetic fibers (e.g. TYVEK®), collagen films, chitosan films, rayon, cellophane, and the like. Suitable webs further include laminates or blends of these materials. Suitable films include both cast and blown. Exemplary thermoplastic films suitable for use as the second substrate are low density polyethylene ("LDPE"), linear low-density polyethylene ("LLDPE"), and blends of LLDPE and LDPE. Films may be apertured.

Substrates can also optionally include colorants, such as pigment, lake, toner, dye, ink, or other agent used to impart a color to a material, to improve the visual appearance of a substrate or the resultant laminate. Suitable pigments herein include inorganic pigments, pearlescent pigments, interference pigments, and the like. Non-limiting examples of suitable pigments include talc, mica, magnesium carbonate, calcium carbonate, magnesium silicate, aluminum magnesium silicate, silica, titanium dioxide, zinc oxide, red iron oxide, yellow iron oxide, black iron oxide, carbon black, ultramarine, polyethylene powder, methacrylate powder, polystyrene powder, silk powder, crystalline cellulose, starch, titanated mica, iron oxide titanated mica, bismuth oxychloride, and the like. Suitable colored webs are described in US 2010/0233438 A1 and US 2010/0233439 A1.

Although the apparatuses and methods have been described in the context of the feminine hygiene article 5 shown in FIGS. 13-15, it is to be appreciated that the methods and apparatuses herein may be used to assemble and bond various substrates and/or elastic laminates that can be used with various process configurations and/or absorbent articles, such as for example, taped diapers or diaper pants.

Figure 16:
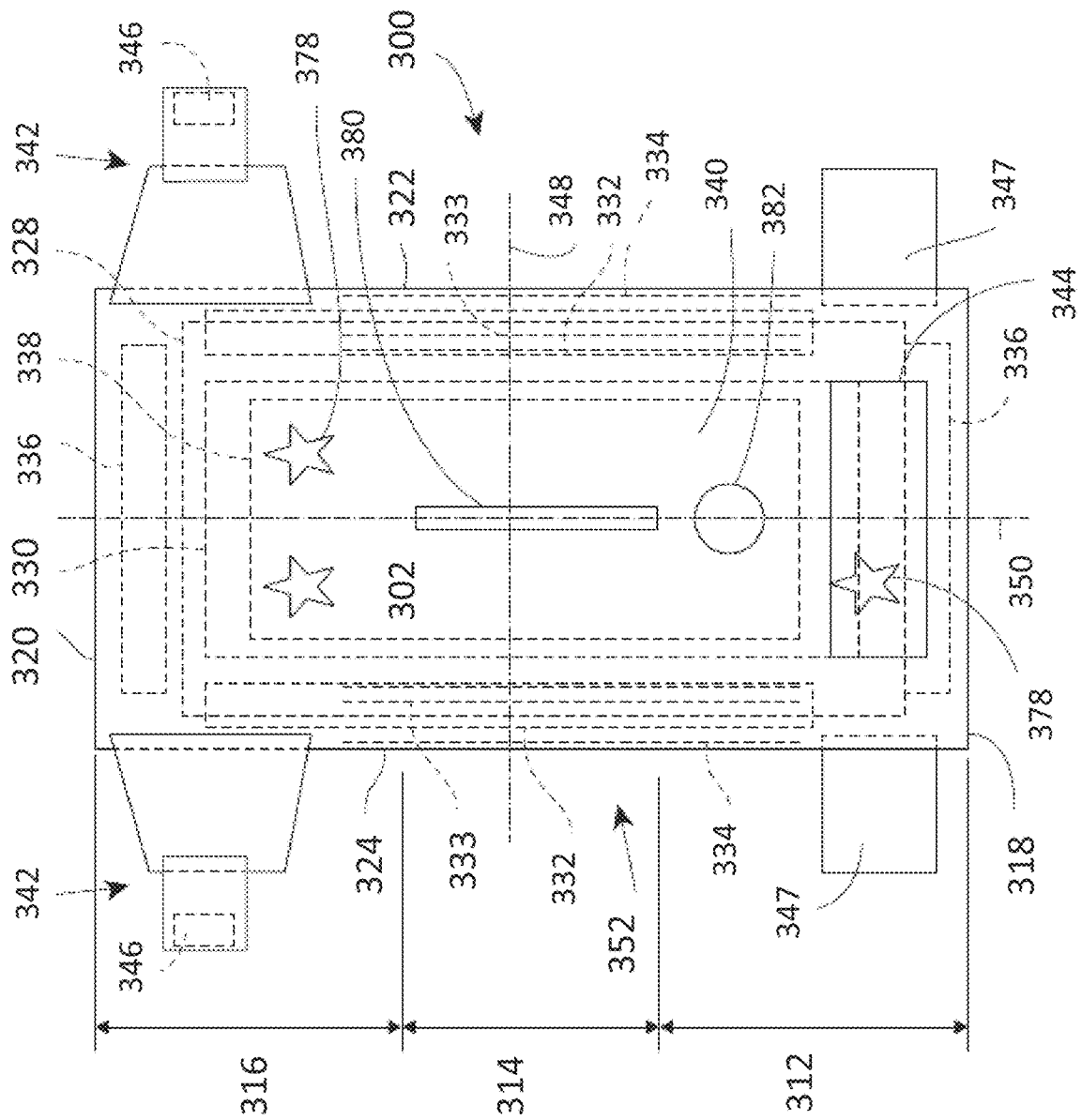
FIG. 16 is a plan view of an example absorbent article in the form of a taped diaper, garment-facing surface facing the viewer, in a flat laid-out state.
Figure 17:
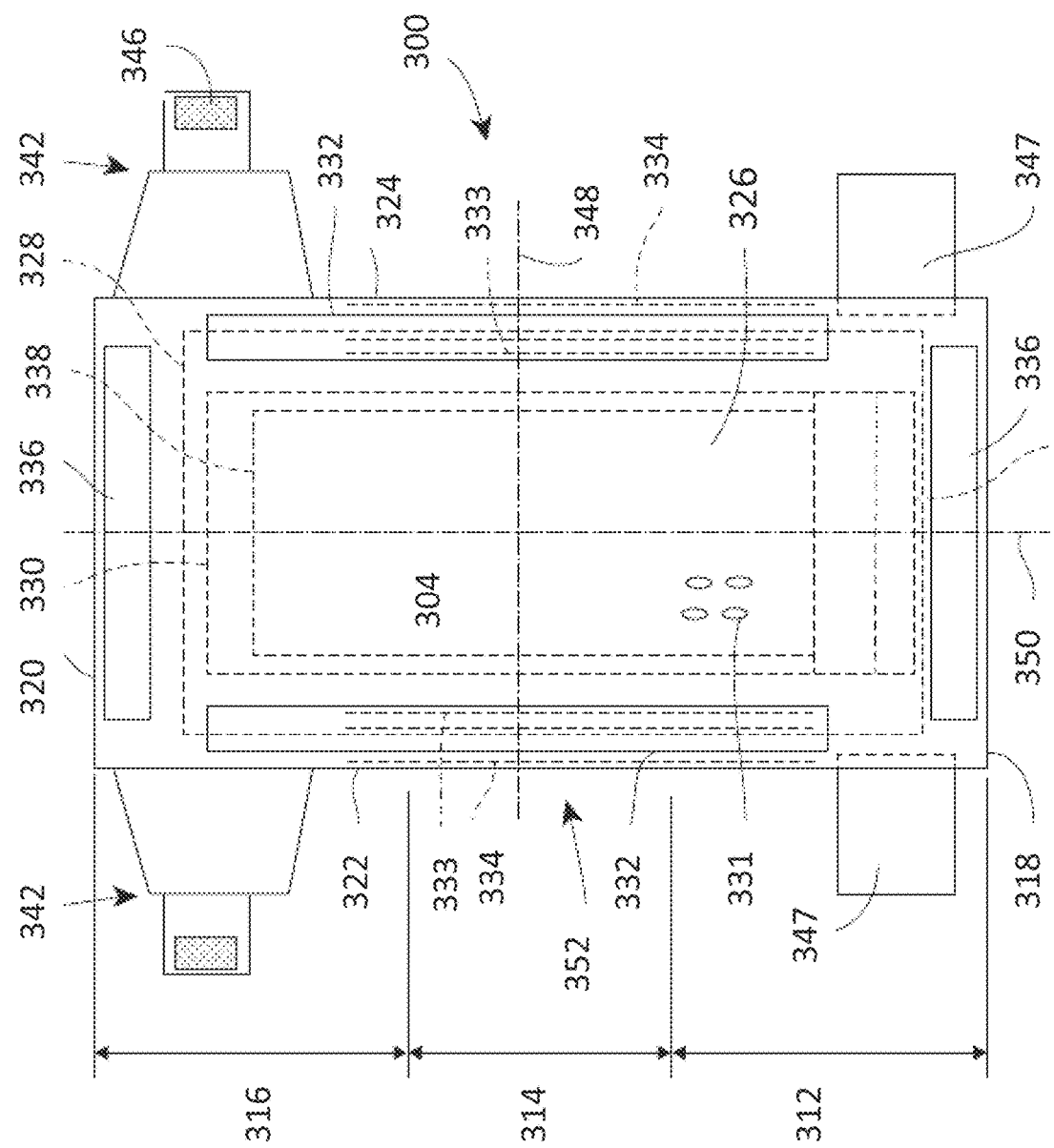
FIG. 17 is a plan view of the example absorbent article of FIG. 16, wearer-facing surface facing the viewer, in a flat laid-out state.
Figure 18:
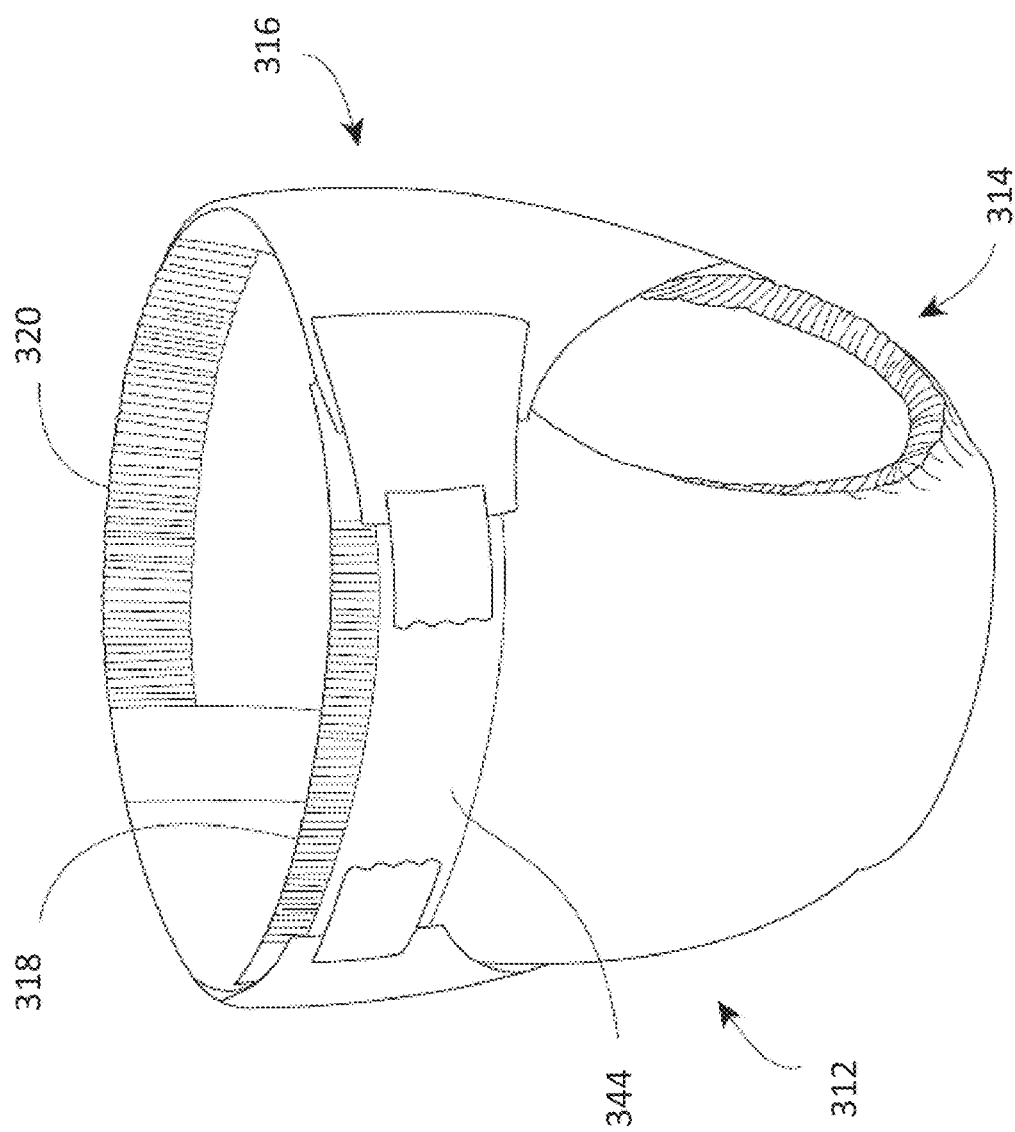
FIG. 18 is a front perspective view of the absorbent article of FIGS. 16 and 17 in a fastened position.

A taped diaper, is represented in FIGS. 16-18. FIG. 16 is a plan view of the example absorbent article 300, garment-facing surface 302 facing the viewer in a flat, laid-out state (i.e., no elastic contraction). The absorbent article 300 may comprise a front waist region 312, a crotch region 314, and a back waist region 316. The crotch region 314 may extend intermediate the front waist region 312 and the back waist region 316. The front waist region 312, the crotch region 314, and the back waist region 316 may each be ⅓ of the length of the absorbent article 300. The absorbent article may comprise a front end edge 318, a back end edge 320 opposite to the front end edge 318, and longitudinally extending, transversely opposed side edges 322 and 324 defined by the chassis 352.

The absorbent article may comprise a liquid permeable topsheet 326, a liquid impermeable backsheet 328, and an absorbent core 330 positioned at least partially intermediate the topsheet and the backsheet. The absorbent article may also comprise one or more pairs of barrier leg cuffs 332 with or without elastics 333, one or more pairs of leg elastics 334, one or more elastic waistbands 336, and/or one or more acquisition materials 338. The acquisition material or materials 338 may be positioned intermediate the topsheet 326 and the absorbent core 330. An outer cover material 340, such as a nonwoven material, may cover a garment-facing side of the backsheet 328. The absorbent article may comprise back ears 342 in the back waist region 316. The back ears 342 may comprise fasteners 346 and may extend from the back waist region 316 of the absorbent article 300 and attach (using the fasteners 346) to the landing zone area or landing zone material 344 on a garment-facing portion of the front waist region 312 of the absorbent article 300. The absorbent article 300 may also have front ears 347 in the front waist region 312. The absorbent article 300 may have a central lateral (or transverse) axis 348 and a central longitudinal axis 350. The central lateral axis 348 extends perpendicular to the central longitudinal axis 350.

Figure 19:
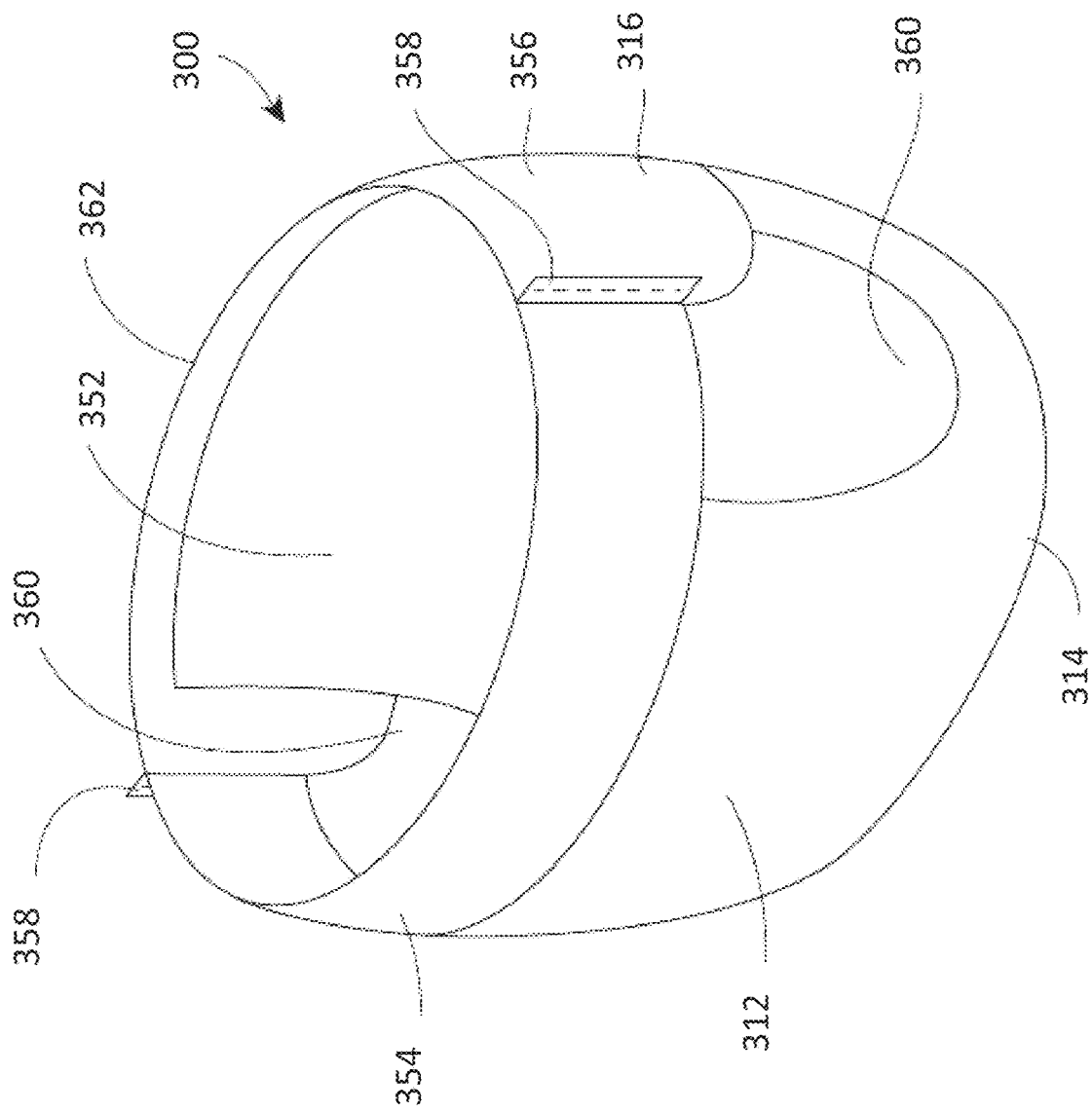
FIG. 19 is a front perspective view of an absorbent article in the form of a pant.
Figure 20:
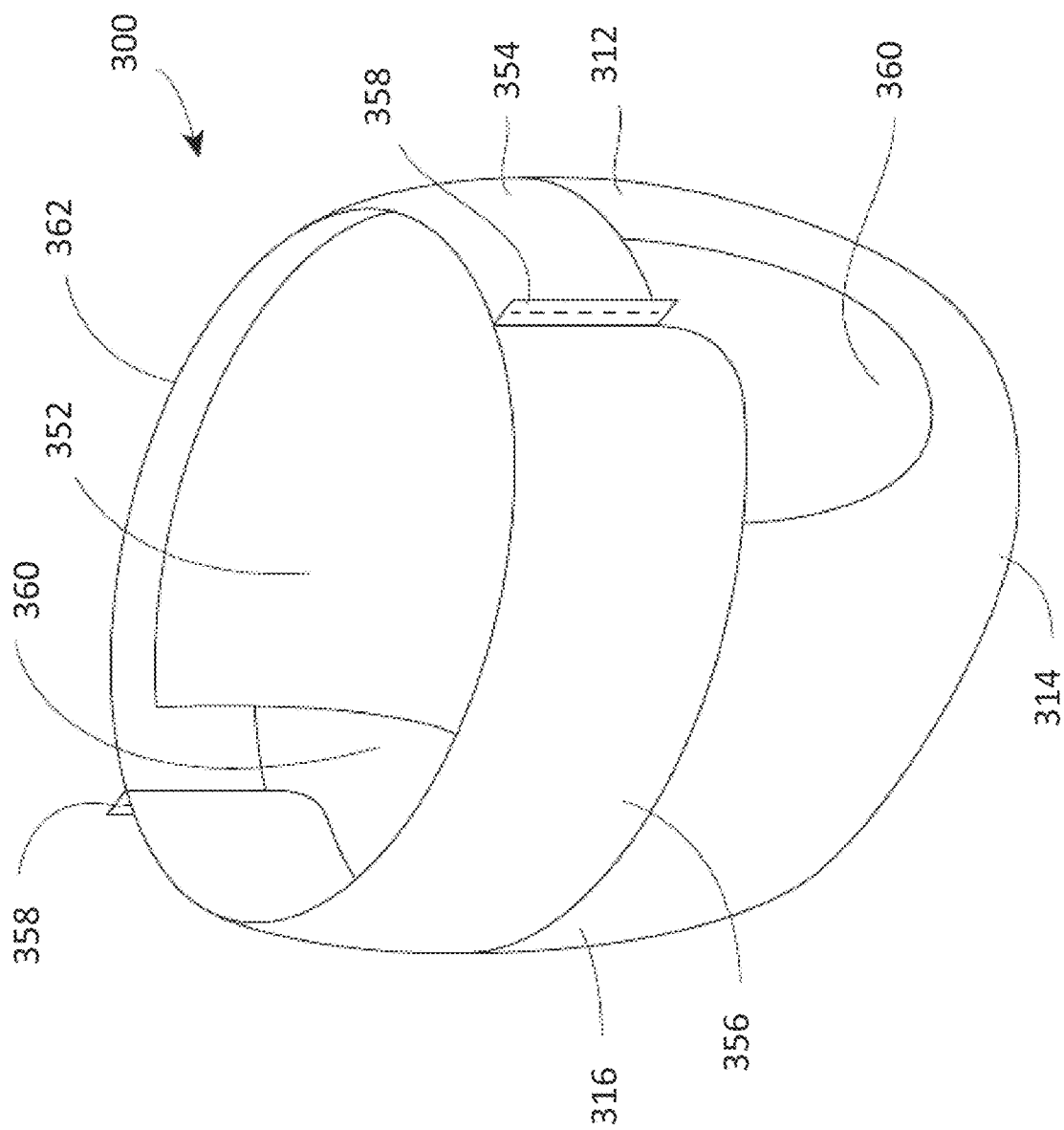
FIG. 20 is a rear perspective view of the absorbent article of FIG. 19.
Figure 21:
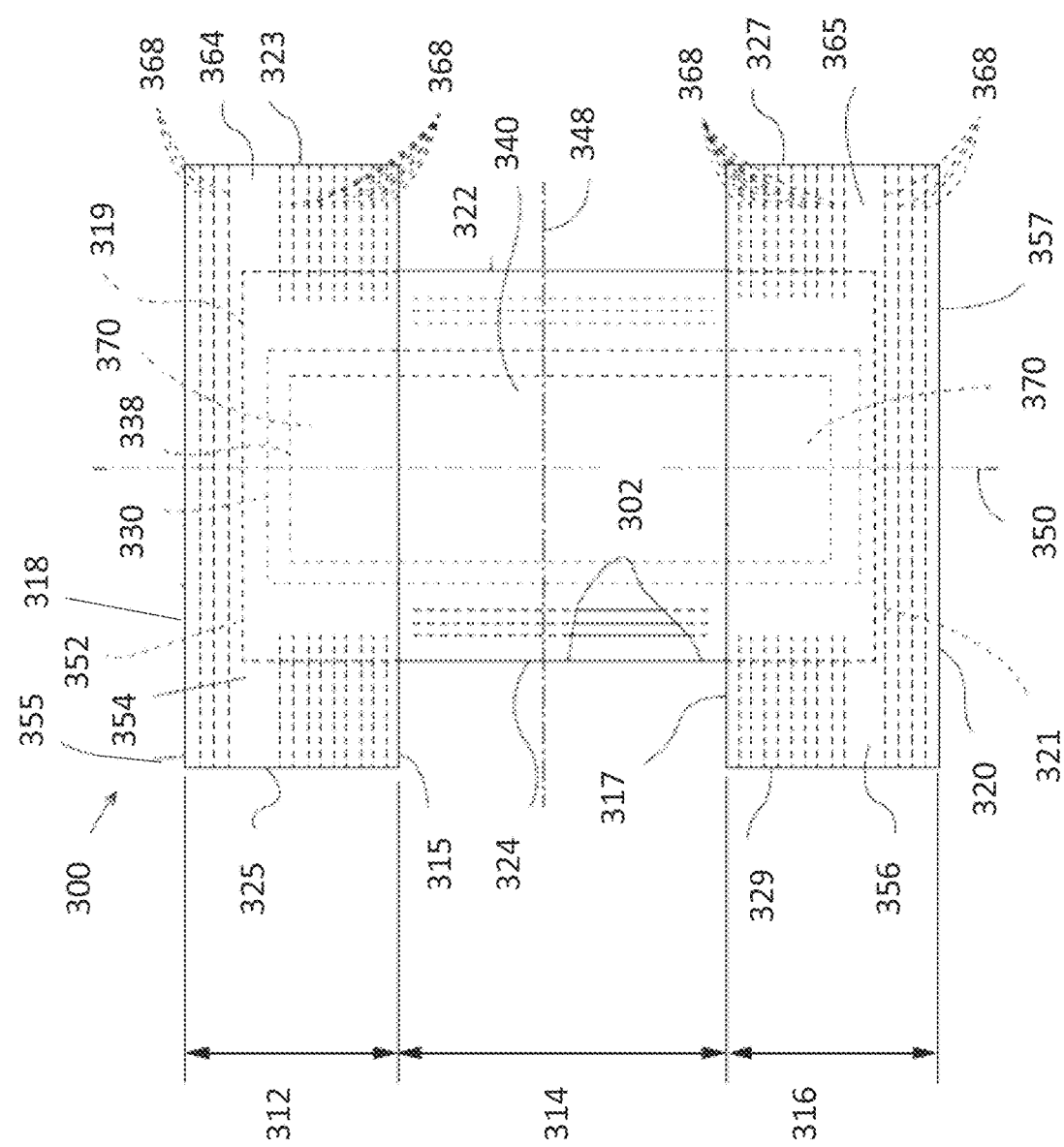
FIG. 21 is a plan view of the absorbent article of FIG. 19, laid flat, with a garment-facing surface facing the viewer.

In other instances, the absorbent article may be in the form of a pant having permanent or refastenable side seams. Suitable refastenable seams are disclosed in U.S. Pat. Appl. Pub. No. 2014/0005020 A1 and U.S. Pat. No. 9,421,137. Referring to FIGS. 19-21, an example absorbent article 300 in the form of a pant is illustrated. FIG. 19 is a front perspective view of the absorbent article 300. FIG. 20 is a rear perspective view of the absorbent article 300. FIG. 21 is a plan view of the absorbent article 300, laid flat, with the garment-facing surface facing the viewer. The absorbent article 300 may have a front waist region 312, a crotch region 314, and a back waist region 316. Each of the regions 312, 314, and 316 may be ⅓ of the length of the absorbent article 300. The absorbent article 300 may have a chassis 352 (sometimes referred to as a central chassis or central panel) comprising a topsheet 326, a backsheet 328, and an absorbent core 330 disposed at least partially intermediate the topsheet 326 and the backsheet 328, and an optional acquisition material 338, similar to that as described above with respect to FIGS. 16-18. The absorbent article may comprise a front belt 354 in the front waist region 312 and a back belt 356 in the back waist region 316. The chassis 352 may be joined to a wearer-facing surface 304 of the front and back belts 354, 356 or to a garment-facing surface 302 of the belts 354, 356. Side edges 323 and 325 of the front belt 354 may be joined to side edges 327 and 329, respectively, of the back belt 356 to form two side seams 358. The side seams 358 may be any suitable seams known to those of skill in the art, such as butt seams or overlap seams, for example. When the side seams 358 are permanently formed or refastenably closed, the absorbent article 300 in the form of a pant has two leg openings 360 and a waist opening circumference 362. The side seams 358 may be permanently joined using adhesives or bonds, for example, or may be refastenably closed using hook and loop fasteners, for example.

The front and back belts 354 and 356 may comprise front and back inner belt layers and front and back outer belt layers having an elastomeric material (e.g., strands or a film (which may be apertured)) disposed at least partially therebetween. The elastic elements or the film may be relaxed (including being cut) to reduce elastic strain over the absorbent core or, may alternatively, run continuously across the absorbent core. The elastics elements may have uniform or variable spacing therebetween in any portion of the belts. The elastic elements may also be pre-strained the same amount or different amounts. The front and/or back belts 354 and 356 may have one or more elastic element free zones where the chassis overlaps the belts 354, 356. In other instances, at least some of the elastic elements may extend continuously across the chassis 352.

The front and back inner belt layers and the front and back outer belt layers, may be joined using adhesives, heat bonds, pressure bonds or thermoplastic bonds. Various suitable belt layer configurations can be found in U.S. Pat. Appl. Pub. No. 2013/0211363 A1.

Front and back belt end edges may extend longitudinally beyond the front and back chassis end edges 319 and 321 (as shown in FIG. 21) or they may be co-terminus. The front and back belt side edges may extend laterally beyond the chassis side edges 322 and 324. The front and back belts 354 and 356 may be continuous (i.e., having at least one layer that is continuous) from belt side edge to belt side edge. Alternatively, the front and back belts 354 and 356 may be discontinuous from belt side edge to belt side edge, such that they are discrete.

As disclosed in U.S. Pat. No. 7,901,393, the longitudinal length (along the central longitudinal axis 350) of the back belt 356 may be greater than the longitudinal length of the front belt 354, and this may be particularly useful for increased buttocks coverage when the back belt has a greater longitudinal length versus the front belt adjacent to or immediately adjacent to the side seams 58.

The front outer belt layer and the back outer belt layer may be separated from each other, such that the layers are discrete or, alternatively, these layers may be continuous, such that a layer runs continuously from the front belt end edge to the back belt end edge. This may also be true for the front and back inner belt layers—that is, they may also be longitudinally discrete or continuous. Further, the front and back outer belt layers may be longitudinally continuous while the front and back inner belt layers are longitudinally discrete, such that a gap is formed between them.

The front and back belts 354 and 356 may include slits, holes, and/or perforations providing increased breathability, softness, and a garment-like texture. Underwear-like appearance can be enhanced by substantially aligning the waist and leg edges at the side seams 358.

The front and back belts 354 and 356 may comprise graphics. The graphics may extend substantially around the entire circumference of the absorbent article 300 and may be disposed across side seams and/or across proximal front and back belt seams; or, alternatively, adjacent to the seams in the manner described in U.S. Pat. No. 9,498,389 to create a more underwear-like article. The graphics may also be discontinuous.

Alternatively, instead of attaching belts and to the chassis to form a pant, discrete side panels may be attached to side edges of the chassis. Suitable forms of pants comprising discrete side panels are disclosed in U.S. Pat. Nos. 6,645, 190; 8,747,379; 8,372,052; 8,361,048; 6,761,711; 6,817, 994; 8,007,485; 7,862,550; 6,969,377; 7,497,851; 6,849,067; 6,893,426; 6,953,452; 6,840,928; 8,579,876; 7,682,349; 7,156,833; and 7,201,744.

The topsheet 326 is the part of the absorbent article 300 that is in contact with the wearer's skin. The topsheet 326 may be joined to portions of the backsheet 328, the absorbent core 330, the barrier leg cuffs 332, and/or any other layers as is known to those of ordinary skill in the art. The topsheet 326 may be compliant, soft-feeling, and non-irritating to the wearer's skin. Further, at least a portion of, or all of, the topsheet may be liquid permeable, permitting liquid bodily exudates to readily penetrate through its thickness. A suitable topsheet may be manufactured from a wide range of materials, such as porous foams, reticulated foams, apertured plastic films, woven materials, nonwoven materials, woven or nonwoven materials of natural fibers (e.g., wood or cotton fibers), synthetic fibers or filaments (e.g., polyester or polypropylene or bicomponent PE/PP fibers or mixtures thereof), or a combination of natural and synthetic fibers. The topsheet may have one or more layers. The topsheet may be apertured (FIG. 17, element 331), may have any suitable three-dimensional features, and/or may have a plurality of embossments (e.g., a bond pattern). The topsheet may be apertured by overbonding a material and then rupturing the overbonds through ring rolling, such as disclosed in U.S. Pat. No. 5,628,097, to Benson et al., issued on May 13, 1997 and disclosed in U.S. Pat. Appl. Publication No. US 2016/0136014 A1 to Arora et al. Any portion of the topsheet may be coated with a skin care composition, an antibacterial agent, a surfactant, and/or other beneficial agents. The topsheet may be hydrophilic or hydrophobic or may have hydrophilic and/or hydrophobic portions or layers. If the topsheet is hydrophobic, typically apertures will be present so that bodily exudates may pass through the topsheet.

The backsheet 328 is generally that portion of the absorbent article 300 positioned proximate to the garment-facing surface of the absorbent core 330. The backsheet 328 may be joined to portions of the topsheet 326, the outer cover material 340, the absorbent core 330, and/or any other layers of the absorbent article by any attachment methods known to those of skill in the art. The backsheet 328 prevents, or at least inhibits, the bodily exudates absorbed and contained in the absorbent core from soiling articles such as bedsheets, undergarments, and/or clothing. The backsheet is typically liquid impermeable, or at least substantially liquid impermeable. The backsheet may, for example, be or comprise a thin plastic film, such as a thermoplastic film having a thickness of about 0.012 mm to about 0.051 mm. Other suitable backsheet materials may include breathable materials which permit vapors to escape from the absorbent article, while still preventing, or at least inhibiting, bodily exudates from passing through the backsheet.

The outer cover material (sometimes referred to as a backsheet nonwoven) 340 may comprise one or more nonwoven materials joined to the backsheet 328 and that covers the backsheet 328. The outer cover material 340 forms at least a portion of the garment-facing surface 302 of the absorbent article 300 and effectively "covers" the backsheet 328 so that film is not present on the garment-facing surface 302. The outer cover material 340 may comprise a bond pattern, apertures, and/or three-dimensional features.

As used herein, the term "absorbent core" 330 refers to the component of the absorbent article having the most absorbent capacity and that comprises an absorbent material. In some instances, absorbent material may be positioned within a core bag or a core wrap. The absorbent material may be profiled or not profiled, depending on the specific absorbent article. The absorbent core 330 may comprise, consist essentially of, or consist of, a core wrap, absorbent material, and glue enclosed within the core wrap. The absorbent material may comprise superabsorbent polymers, a mixture of superabsorbent polymers and air felt, only air felt, and/or a high internal phase emulsion foam. In some instances, the absorbent material may comprise at least 80%, at least 85%, at least 90%, at least 95%, at least 99%, or up to 100% superabsorbent polymers, by weight of the absorbent material. In such instances, the absorbent material may be free of air felt, or at least mostly free of air felt. The absorbent core periphery, which may be the periphery of the core wrap, may define any suitable shape, such as rectangular "T," "Y," "hour-glass," or "dog-bone" shaped, for example. An absorbent core periphery having a generally "dog bone" or "hour-glass" shape may taper along its width towards the crotch region 314 of the absorbent article 300.

The absorbent core 330 may have areas having little or no absorbent material, where a wearer-facing surface of the core bag may be joined to a garment-facing surface of the core bag. These areas having little or no absorbent material may be referred to as channels. These channels can embody any suitable shapes and any suitable number of channels may be provided. In other instances, the absorbent core may be embossed to create the impression of channels.

Referring to FIGS. 16 and 17, for example, the absorbent article 300 may comprise one or more pairs of barrier leg cuffs 332 and one or more pairs of leg elastics 334. The barrier leg cuffs 332 may be positioned laterally inboard of leg elastics 334. Each barrier leg cuff 332 may be formed by a piece of material which is bonded to the absorbent article 300 so it can extend upwards from a wearer-facing surface 304 of the absorbent article 300 and provide improved containment of body exudates approximately at the junction of the torso and legs of the wearer. The barrier leg cuffs 332 are delimited by a proximal edge joined directly or indirectly to the topsheet and/or the backsheet and a free terminal edge, which is intended to contact and form a seal with the wearer's skin. The barrier leg cuffs 332 may extend at least partially between the front end edge 318 and the back end edge 320 of the absorbent article 300 on opposite sides of the central longitudinal axis 350 and may be at least present in the crotch region 314. The barrier leg cuffs 332 may each comprise one or more elastics 333 (e.g., elastic strands or strips) near or at the free terminal edge. These elastics 333 cause the barrier leg cuffs 332 to help form a seal around the legs and torso of a wearer. The leg elastics 334 extend at least partially between the front end edge 318 and the back end edge 320. The leg elastics 334 essentially cause portions of the absorbent article 300 proximate to the chassis side edges 322, 324 to help form a seal around the legs of the wearer. The leg elastics 334 may extend at least within the crotch region 14.

Referring to FIGS. 16 and 17, the absorbent article 300 may comprise one or more elastic waistbands 336. The elastic waistbands 336 may be positioned on the garment-facing surface 302 or the wearer-facing surface 304. As an example, a first elastic waistband 336 may be present in the front waist region 312 near the front belt end edge 318 and a second elastic waistband 336 may be present in the back waist region 316 near the back end edge 320. The elastic waistbands 336 may aid in sealing the absorbent article 300 around a waist of a wearer and at least inhibiting bodily exudates from escaping the absorbent article 300 through the waist opening circumference. In some instances, an elastic waistband may fully surround the waist opening circumference of an absorbent article.

One or more acquisition materials 338 may be present at least partially intermediate the topsheet 326 and the absorbent core 330. The acquisition materials 338 are typically hydrophilic materials that provide significant wicking of bodily exudates. These materials may dewater the topsheet 326 and quickly move bodily exudates into the absorbent core 330. The acquisition materials 338 may comprise one or more nonwoven materials, foams, cellulosic materials, cross-linked cellulosic materials, air laid cellulosic nonwoven materials, spunlace materials, or combinations thereof, for example. In some instances, portions of the acquisition materials 338 may extend through portions of the topsheet 326, portions of the topsheet 326 may extend through portions of the acquisition materials 338, and/or the topsheet 326 may be nested with the acquisition materials 338. Typically, an acquisition material 338 may have a width and length that are smaller than the width and length of the topsheet 326. The acquisition material may be a secondary topsheet in the feminine pad context. The acquisition material may have one or more channels as described above with reference to the absorbent core 330 (including the embossed version). The channels in the acquisition material may align or not align with channels in the absorbent core 330. In an example, a first acquisition material may comprise a nonwoven material and as second acquisition material may comprise a cross-linked cellulosic material.

Referring to FIGS. 16 and 17, the absorbent article 300 may have a landing zone area 344 that is formed in a portion of the garment-facing surface 302 of the outer cover material 340. The landing zone area 344 may be in the back waist region 316 if the absorbent article fastens from front to back or may be in the front waist region 312 if the absorbent article fastens back to front. In some instances, the landing zone 344 may be or may comprise one or more discrete nonwoven materials that are attached to a portion of the outer cover material 340 in the front waist region 312 or the back waist region 316 depending upon whether the absorbent article fastens in the front or the back. In essence, the landing zone 344 is configured to receive the fasteners 346 and may comprise, for example, a plurality of loops configured to be engaged with, a plurality of hooks on the fasteners 346, or vice versa.

Referring to FIG. 16, the absorbent articles 300 of the present disclosure may comprise graphics 378 and/or wetness indicators 380 that are visible from the garment-facing surface 302. The graphics 378 may be printed on the landing zone 340, the backsheet 328, and/or at other locations. The wetness indicators 830 are typically applied to the absorbent core facing side of the backsheet 328, so that they can be contacted by bodily exudates within the absorbent core 330. In some instances, the wetness indicators 380 may form portions of the graphics 378. For example, a wetness indicator may appear or disappear and create/remove a character within some graphics. In other instances, the wetness indicators 380 may coordinate (e.g., same design, same pattern, same color) or not coordinate with the graphics 378.

Referring to FIGS. 16 and 17, as referenced above, the absorbent article 300 may have front and/or back ears 347, 342 in a taped diaper context. Only one set of ears may be required in most taped diapers. The single set of ears may comprise fasteners 346 configured to engage the landing zone or landing zone area 344. If two sets of ears are provided, in most instances, only one set of the ears may have fasteners 346, with the other set being free of fasteners.

The ears, or portions thereof, may be elastic or may have elastic panels. In an example, an elastic film or elastic strands may be positioned intermediate a first nonwoven material and a second nonwoven material. The elastic film may or may not be apertured. The ears may be shaped. The ears may be integral (e.g., extension of the outer cover material 340, the backsheet 328, and/or the topsheet 326) or may be discrete components attached to a chassis 352 of the absorbent article on a wearer-facing surface 304, on the garment-facing surface 302, or intermediate the two surfaces 304, 302.

Referring again to FIG. 16, the absorbent articles of the present disclosure may comprise a sensor system 382 for monitoring changes within the absorbent article. The sensor system 382 may be discrete from or integral with the absorbent article 300. The absorbent article may comprise sensors that can sense various aspects of the absorbent article associated with insults of bodily exudates such as urine and/or BM (e.g., the sensor system 382 may sense variations in temperature, humidity, presence of ammonia or urea, various vapor components of the exudates (urine and feces), changes in moisture vapor transmission through the absorbent articles garment-facing layer, changes in translucence of the garment-facing layer, and/or color changes through the garment-facing layer). Additionally, the sensor system 382 may sense components of urine, such as ammonia or urea and/or byproducts resulting from reactions of these components with the absorbent article 300. The sensor system 382 may sense byproducts that are produced when urine mixes with other components of the absorbent article 300 (e.g., adhesives, agm). The components or byproducts being sensed may be present as vapors that may pass through the garment-facing layer. It may also be desirable to place reactants in the absorbent article that change state (e.g. color, temperature) or create a measurable byproduct when mixed with urine or BM. The sensor system 382 may also sense changes in pH, pressure, odor, the presence of gas, blood, a chemical marker or a biological marker or combinations thereof. The sensor system 382 may have a component on or proximate to the absorbent article that transmits a signal to a receiver more distal from the absorbent article, such as an iPhone, for example. The receiver may output a result to communicate to the caregiver a condition of the absorbent article 300. In other instances, a receiver may not be provided, but instead the condition of the absorbent article 300 may be visually or audibly apparent from the sensor on the absorbent article.

Other materials that may be considered substrates, or include substrates as a part of a final product. Substrates may include films. Suitable films include water-soluble or water-dispersible films. The films may be thermo-formable and/or vacuum-formable. The film may include polymeric materials. Suitable polymeric materials include polyvinyl alcohols, hydroxypropyl methyl cellulose (HPMC), copolymers thereof, derivatives thereof, or combinations thereof. The film may further include one or more additive ingredients, such as plasticizer, surfactant, cleaning additives, water, or other suitable adjuncts. The films may be obtained by casting, blow-molding, extrusion or blown extrusion of the polymeric material, as known in the art. The film may have a thickness of from about 20 to 150 microns, or from about 50 to 110 microns. Suitable water-soluble films may include those supplied by MonoSol, LLC (Merrillville, Ind., USA) under the trade references M8630, M8900, M8779, M9467, and M8310, as well as films, such as PVA films, having corresponding solubility, deformability, and/or sealing characteristics. Suitable films are also described in U.S. Pat. Nos.

6,166,117, 6,787,512, US 2006/0213801 A1, WO 2010/119022, US 2011/0186468 A1, and US 2011/0188784 A1.

The films may be formed, for example by thermoforming and/or vacuum-forming, into unitized dose pouches, such as single- or multi-compartment pouches. One or more films may be formed into a web of sealed compartments via a continuous or a discontinuous process, and the web may be cut to form individual pouches. The pouches may contain a composition, such as a fabric care or hard surface care composition. Such compositions may be in the form of liquid, gel, solid, granular, or combinations thereof. Suitable pouches and processes for making such pouches are described in WO 2002/042408 and WO 2009/098659. Commercially available pouches include those marketed as TIDE PODS, GAIN FLINGS, and CASCADE ACTIONPACS (each available from The Procter & Gamble Company, Cincinnati, Ohio, USA).

Further, substrates may be used in cleaning products. For example, a duster cleaning article may comprise a nonwoven sheet having tow fibers joined thereto. The cleaning article may have a longitudinal axis. The tow fibers may be joined to the nonwoven sheet in a generally transverse direction and particularly in a direction normal the longitudinal axis, to provide a laminate structure of two layers.

If desired, the cleaning article may comprise additional layers, also referred to herein as laminae. For example, the tow fibers may be disposed intermediate two nonwoven sheets. Plural laminae of tow fibers may be disposed intermediate the nonwoven sheets and/or outboard thereof. Optionally, one or more of the nonwoven sheets may be cut to comprise strips. The strips may be generally normal to the longitudinal axis.

The tow fibers and/or nonwoven sheets may comprise an additive to assist in removal of dust and other debris from the target surface. The additive may comprise wax, such as microcrystalline wax, oil, adhesive and combinations thereof. The cleaning article may be made according to U.S. Pat. No. 6,813,801 and according to commonly assigned U.S. Pat. Nos. 7,803,726; 8,756,746; 8,763,197 and 8,931,132.

The laminae of the cleaning article may be joined together using adhesive, thermal bonding, ultrasonic welding, etc. If desired, the bonding lines may be generally parallel to the longitudinal axis and may be continuous, or discontinuous as desired. Three longitudinally parallel bonding lines may be utilized to define two sleeves.

The two sleeves may accept one or more complementary fork tines of a handle. The fork tines may be removably inserted into the sleeves of the cleaning article to provide for improved ergonomics. The handle may be plastic and made according to the teachings of U.S. Pat. Nos. 7,219,386; 7,293,317, 7,383,602 and/or commonly assigned U.S. Pat. No. 8,578,564. Representative dusters are sold by the instant assignee under the name SWIFFER®.

Further still, substrates may include cleaning sheets. The cleaning sheet may comprise a nonwoven. The nonwoven may be synthetic and/or have cellulosic fibers therein. The synthetic fibers may comprise carded, staple, wet laid, air laid and/or spunbond fibers. The nonwoven cleaning sheet may be made according to a hydro-entangling process to provide a texture and a basis weight of about 20 to about 120 g/m$^2$.

Optionally, the cleaning sheet may further comprise an additive, to improve cleaning performance and/or enhance the cleaning experience. The additive may comprise wax, such as microcrystalline wax, oil, adhesive, perfume and combinations thereof. The cleaning sheet according to the present invention may be made according to commonly assigned U.S. Pat. Nos. 6,305,046; 6,484,346; 6,561,354; 6,645,604; 6,651,290; 6,777,064; 6,790,794; 6,797,357; 6,936,330; D409,343; D423,742; D489,537; D498,930; D499,887; D501,609; D511,251 and/or D615,378.

In some embodiments, the cleaning sheet may comprise layers, to provide for absorption and storage of cleaning fluid deposited on the target surface. If desired, the cleaning sheet may comprise absorbent gelling materials to increase the absorbent capacity of the cleaning sheet. The absorbent gelling materials may be distributed within the cleaning sheet in such a manner to avoid rapid absorbency and absorb fluids slowly, to provide for the most effective use of the cleaning sheet.

The cleaning sheet may comprise plural layers disposed in a laminate. The lowest, or downwardly facing outer layer, may comprise apertures to allow for absorption of cleaning solution therethrough and to promote the scrubbing of the target surface. Intermediate layers may provide for storage of the liquids, and may comprise the absorbent gelling materials. The cleaning sheet may have an absorbent capacity of at least 10, 15, or 20 grams of cleaning solution per gram of dry cleaning sheet, as set forth in commonly assigned U.S. Pat. Nos. 6,003,191 and 6,601,261.

The top or upwardly facing outer layer, maybe liquid impervious in order to minimize loss of absorbed fluids. The top layer may further provide for releasable attachment of the cleaning sheet to a cleaning implement. The top layer may be made of a polyolefinic film, such as LDPE.

This application claims the benefit of U.S. Provisional Application No. 62/595,606, filed on Dec. 7, 2017, the entirety of which is incorporated by reference herein.

All publications, patent applications, and issued patents mentioned herein are hereby incorporated in their entirety by reference. Citation of any reference is not an admission regarding any determination as to its availability as prior art to the claimed invention.

The dimensions and/or values disclosed herein are not to be understood as being strictly limited to the exact numerical values recited. Instead, unless otherwise specified, each such dimension and/or value is intended to mean both the recited dimension and/or value and a functionally equivalent range surrounding that dimension and/or value. For example, a dimension disclosed as "40 mm" is intended to mean "about 40 mm".

While particular embodiments of the present invention have been illustrated and described, it would be obvious to those skilled in the art that various other changes and modifications may be made without departing from the spirit and scope of the invention. It is therefore intended to cover in the appended claims all such changes and modifications that are within the scope of this invention.

What is claimed is:

1. A compression method for forming a bond, the method comprising:
rotating a bonding roll about an axis of rotation, the bonding roll comprising a compliant first pressure applying member comprising a base surface and a bonding surface with a first spring element positioned therebetween to provide a reduced stiffness zone, said member extending radially outward from the bonding roll;
rotating an anvil roll adjacent the bonding roll such that a nip is formed between the bonding roll and the anvil roll;
advancing a first substrate in a machine direction through the nip;

rotating the bonding roll and the anvil roll wherein the first pressure applying member compresses at least a portion of the first substrate forming a bond; and compressing the first pressure applying member by a first compression distance, whereby said pressure reaches the yield strength of the substrate to form a bond, but does not reach the ultimate strength of said substrate.

2. The method of claim 1, wherein the bonding roll comprises a second pressure applying member having a second spring element.

3. The method of claim 2, wherein the first spring element of the first pressure applying member has a first spring constant and the second spring element of the second pressure applying member has a second spring constant, wherein the first spring constant and the second spring constant are different.

4. The method of claim 2, wherein the first spring element of the first pressure applying member has a first spring constant and the second spring element of the second pressure applying member has a second spring constant, wherein the first spring constant and the second spring constant are the same.

5. The method of claim 2, wherein each of the first pressure applying member and the second pressure applying member produces forces that vary non-linearly with displacement.

6. The method of claim 1, comprising:

advancing a second substrate in the machine direction through the nip;

overlapping at least a portion of the first substrate with at least a portion of the second substrate forming an overlap portion; and operatively engaging an outer circumferential surface of the anvil roll and a bonding surface of the first pressure applying member to form a bond in the overlap portion.

7. The method of claim 2, comprising compressing the second pressure applying member by a second compression distance, wherein the first compression distance is different than the second compression distance.

8. The method of claim 1, wherein the first compression distance is greater than about $1 \times 10^{-9}$ m.

9. The method of claim 1, wherein the substrate comprising one or more bonds is a component of an absorbent article.

10. The method of claim 1, wherein the substrate is a film.

11. The method of claim 10, wherein the film forms at least a portion of a pouch.

12. The method of claim 1, wherein the substrate comprising one or more bonds forms a portion of a cleaning product.

* * * * *